United States Patent
Burbank

(10) Patent No.: US 10,201,373 B2
(45) Date of Patent: Feb. 12, 2019

(54) CARTRIDGE FOR NEUROMONITORING NEEDLE-CARTRIDGE GUN SYSTEM

(71) Applicant: John E Burbank, Ridgefield, CT (US)

(72) Inventor: John E Burbank, Ridgefield, CT (US)

(73) Assignees: Payam Andalib, Storrs Mansfield, CT (US); Joseph Haddad, III, Glastonbury, CT (US)

( * ) Notice: Subject to any disclaimer, the term of this patent is extended or adjusted under 35 U.S.C. 154(b) by 0 days.

(21) Appl. No.: 15/690,813

(22) Filed: Aug. 30, 2017

(65) Prior Publication Data

US 2018/0000515 A1    Jan. 4, 2018

Related U.S. Application Data

(62) Division of application No. 14/176,109, filed on Feb. 9, 2014, now Pat. No. 9,782,200.

(51) Int. Cl.
| | |
|---|---|
| A61B 5/04 | (2006.01) |
| A61B 17/34 | (2006.01) |
| A61B 5/00 | (2006.01) |
| A61B 5/0492 | (2006.01) |
| A61N 1/05 | (2006.01) |
| A61B 17/29 | (2006.01) |
| A61B 50/30 | (2016.01) |

(52) U.S. Cl.
CPC ...... *A61B 17/3468* (2013.01); *A61B 5/04001* (2013.01); *A61B 5/0492* (2013.01); *A61B 5/6849* (2013.01); *A61B 50/3001* (2016.02); *A61N 1/0502* (2013.01); *A61N 1/0551* (2013.01); *A61B 2017/2923* (2013.01); *A61B 2050/3007* (2016.02)

(58) Field of Classification Search
CPC .................................................. A61N 1/0502
See application file for complete search history.

(56) References Cited

U.S. PATENT DOCUMENTS

| | | | |
|---|---|---|---|
| 3,841,310 A | 10/1974 | Goldstein | |
| 4,380,234 A | 4/1983 | Kamen | |
| 4,518,384 A | 5/1985 | Tarello | |
| 5,211,175 A * | 5/1993 | Gleason | A61N 1/36017 128/907 |
| 5,522,797 A | 6/1996 | Grimm | |
| 6,258,056 B1 | 7/2001 | Turley | |
| 6,516,226 B1 | 2/2003 | Bishay | |
| 6,783,002 B1 | 8/2004 | Pavlo | |
| 8,631,993 B2 | 2/2014 | Kostrzewski | |

(Continued)

OTHER PUBLICATIONS

Upstate Medical University, Interoperative Neuro-Monitoring Needle Safety Flap.

*Primary Examiner* — Luther G Behringer
(74) *Attorney, Agent, or Firm* — Robert S. Smith

(57) ABSTRACT

A neuromonitoring needle electrode placement gun which includes a housing, at least a first needle electrode and housing assembly, an elongated channel dimensioned and configured for accommodating axial movement of the at least a first needle electrode and housing assembly within the channel and for directing movement of the at least a first needle electrode and housing assembly and a pusher dimensioned and configured for engaging the at least a first needle electrode and housing assembly and for axially displacing the at least a first needle electrode and housing assembly.

8 Claims, 35 Drawing Sheets

(56) References Cited

U.S. PATENT DOCUMENTS

| | | |
|---|---|---|
| 2004/0054273 A1 | 3/2004 | Finneran |
| 2005/0096717 A1 | 5/2005 | Bishay |
| 2006/0206164 A1* | 9/2006 | Gavronsky .......... A61H 39/002 607/46 |
| 2009/0036903 A1 | 2/2009 | Ino |
| 2011/0288618 A1 | 11/2011 | Glenn |
| 2012/0226122 A1 | 9/2012 | Meuniot |
| 2012/0273548 A1 | 11/2012 | Ma |
| 2015/0126842 A1 | 5/2015 | Padalino |

* cited by examiner

Fig. 6A
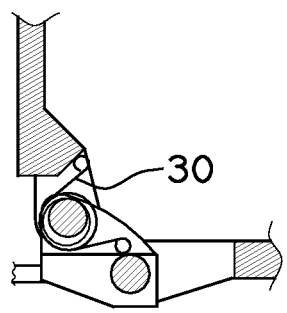
SECTION DETAIL
SPRING ACTUATED ROTATION
OF TOP WING
Fig. 6B
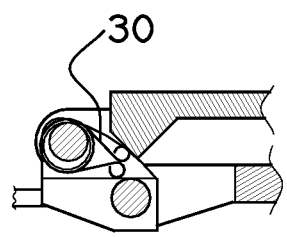
SECTION DETAIL
SPRING LOADING
OF TOP WING
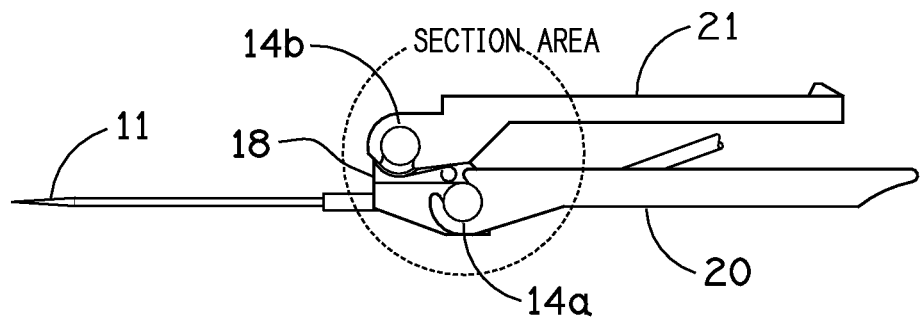
Fig. 6C

CARTRIDGE FOR NEUROMONITORING NEEDLE-CARTRIDGE GUN SYSTEM

RELATED APPLICATIONS

This application is a division of United States patent application entitled NEUROMONITORING NEEDLE-CARTRIDGE GUN SYSTEM having an application Ser. No. 14/176,109, a filing date of Feb. 9, 2014 and which matured into U.S. Pat. No. 9,782,200 on Oct. 10, 2017.

TECHNICAL FIELD

Intraoperative neurophysiological monitoring (IONM) is a real-time assessment of neurological function involving the brain, spinal cord and related nerve structures. IONM facilitates the surgical process and reduces surgical risk by enabling a neurotechnologist (NT) to alert the surgeon if and when spinal cord or neural structure compromise appears imminent. Neuromonitoring is used for spine surgeries, as well as other types of surgical procedures such as craniotomies, total hip replacement and vascular procedures. The purpose of IONM is to reduce the risk to the patient of iatrogenic damage to the nervous system, and/or to provide functional guidance to the surgeon and anesthesiologist. IONM techniques have significantly reduced the rates of morbidity and mortality without introducing additional risks. By doing so, IONM techniques reduce health care costs, To accomplish these objectives, a member of the surgical team with special training in neurophysiology obtains triggered and spontaneous electrophysiologic signals from the patient periodically or continuously throughout the course of the operation. Patients who benefit from neuromonitoring are those undergoing operations involving the nervous system or which pose risk to its anatomic or physiologic integrity. In general, a trained neurophysiologist attaches a computer system to the patient using stimulating and recording electrodes. Interactive software running on the system carries out two tasks:

1. Selective activation of stimulating electrodes with appropriate timing, and
2. Processing and displaying of the electrophysiologic signals as they are picked up by the recording electrodes.

IONM records impulses generated by electrical stimulation of peripheral nerves and dermatomes. Using the International EEG 10-20 electrode placement system, cortical needle electrodes are precisely placed subcutaneously to record sensory responses at specific locations associated with the spinal column and along the course of related peripheral nerves.

Data generated by intraoperative neurophysiological monitoring (IONM) provides a measurement of latency (time it takes for a nerve impulse to travel from a specific point of stimulation to a specific recording site), amplitude (strength of that impulse), and wave form definition. These recordings are called somatosensory and dermatome evoked potentials.

Needle electrodes are inserted into associated muscle groups to monitor spontaneous and electrically evoked myogenic activity. More particularly, in a typical procedure the neurotechnologist (NT) applies multiple stimulating surface electrodes in the pre-operative holding area. Sterile subdermal and intramuscular needle electrodes are inserted after induction and approval of the anesthesiologist. This process is done such that preparation of the patient continues unimpeded. The type of surgery will dictate the number of attached electrodes, which can vary significantly from 15 to 60.

The present invention is generally directed to a system for applying neuromonitoring needles to a patient and the means to connect to monitoring equipment.

BACKGROUND OF THE INVENTION

Intraoperative Neuromonitoring is used during surgery in or near the central or peripheral nervous system. It provides a valuable tool for assessing the integrity of certain neurologic pathways/tracts of a patient during surgery. Such monitoring helps in early identification of adverse events intraoperatively as well as providing a valuable tool for assessing the integrity of certain neurologic pathways/tracts of a patient during surgery. The monitoring typically requires placement of 16-32 subdermal needle electrodes in a patient.

Patients benefit from neuromonitoring during certain surgical procedures, namely any surgery where there is risk to the nervous system. Most neuromonitoring is utilized by spine surgeons or neurosurgeons, but vascular, orthopedic, otolarygologists and urology surgeons have all utilized neuromonitoring as well.

Neuromonitoring utilizes subdermal needle electrodes that are shallowly placed in the patient. The needles remain in place during surgery and are removed after the operation. Patients are often repositioned for transport or other reasons while needles are still in place.

Needle tips can reemerge during moving, repositioning, and handling of the patient. Needle sticks, are a general problem in such procedures. There are an estimated 3.5 million needle sticks worldwide annually. The cost for remediation of each needle stick injury is estimated to be about $2,500. The Needle stick Safety and Prevention Act signed into law on Nov. 6, 2000 revised the Occupational Safety and Health Administration's (OSHA) standard regulating occupational exposure to blood borne pathogens, including the human immunodeficiency virus, the hepatitis B virus, and the hepatitis C virus.

From the above, it is therefore seen that there exists a need in the art to overcome the deficiencies and limitations described herein and above.

SUMMARY OF THE INVENTION

It is an object of the present invention to minimize the risk of needle sticks during implant in the patient, during implant in the patient and withdrawal from the patient.

It is another object of the present invention to more rapidly and precisely implant neuromonitoring needles.

It is yet another object of the present invention to eliminate many of the conventional additional materials and procedures for securing needles to the patient.

It is a still further object of the present invention to assure safety and ease of needle disposal after withdrawal from the patient by automatically providing structure to minimize human exposure to the needles after withdrawal.

It is still another object of the present invention to provide a complete integrated needle delivery system for use at an operating site that is ready to function without additional preparation other than removing the system from a single sterile package.

Additional features and advantages are realized through the techniques of the present invention. Other embodiments and aspects of the invention are described in detail herein and are considered a part of the claimed invention.

The recitation herein of desirable objects which are met by various embodiments of the present invention is not meant to imply or suggest that any or all of these objects are present as essential features, either individually or collectively, in the most general embodiment of the present invention or in any of its more specific embodiments.

It has now been found that one form of the present invention includes a neuromonitoring needle electrode placement gun which includes a housing, an elongated channel having an axis and an axial extremity which is a discharge end, the elongated channel has an interior dimensioned and configured for receiving a plurality of associated needle electrode cartridges. Each includes at least one needle electrode having an exposed point and the plurality of associated needle electrode cartridges are each disposed at axially successive positions along the axis within the elongated channel with each of the exposed points extending toward the discharge end. The elongated channel is carried by the housing and a trigger is mounted for pivotal movement on the housing and a pusher cooperates with the trigger. The pusher is dimensioned and configured for engaging an associated needle electrode cartridge within the plurality of associated needle electrode cartridges that is nearest to the discharge end.

In one embodiment the neuromonitoring needle electrode placement gun further includes a cassette having a plurality of shelves carried by the housing. The shelves are dimensioned and configured for receiving associated coils of wire attached respectively to each of the needle electrode cartridges.

Other forms of the present invention further include a cartridge for cooperation with an associated neuromonitoring needle electrode placement gun which includes a housing; at least one elongated needle electrode, having an axial extent and having a pointed axial extremity, carried by the housing as well as at least a first generally planar wing having first and second faces thereof. The first generally planar wing is carried by the housing in some embodiments.

Some embodiments of the cartridge further include at least a first generally planar wing that is coated with a releasable adhesive on a first face thereof. The cartridge may have engagement surfaces disposed on opposed sides thereof, the engagement surfaces may be dimensioned and configured for cooperation with an elongated track in the associated neuromonitoring needle electrode placement gun. Each cartridge may further include a wire fixed to the at least one needle electrode for conducting either a stimulus for a patient or a patient's response to a stimulus. Each needle electrode may have insulation surrounding an axial portion of the axial extent of the at least one elongated needle electrode and insulation may surround an axial portion of the axial extent of the at least one elongated needle electrode that is spaced a predetermined distance from the pointed axial extremity. The cartridge may further include a second elongated needle electrode having an axial extent and having a pointed axial extremity carried by the housing and the first and second elongated needle electrodes may be disposed in coplanar relationship. In addition the first and second elongated needle electrodes may have the respective pointed axial extremities thereof disposed in perpendicular relationship to and abutting a virtual line that is coplanar with the first and second elongated needle electrodes.

The first and second elongated needle electrodes in some embodiments are spaced apart a distance corresponding to a distance suitable for a differential amplifier to obtain an optimal response from the needle electrodes. In some embodiments both needles in a given pair may measure spontaneous myogenic activity. In other embodiments one needle in a given pair may provide a stimulus and the other needle in the pair may be used to measure evoked myogenic activity. The respective engagement surfaces may be dimensioned and configured for engagement with associated elongated channels in an associated neuromonitoring needle placement gun. Each cartridge may further include a second generally planar wing having first and second faces, the second generally planar wing may also be carried by the housing.

The cartridge may have the first and second generally planar wings carried on the housing by a pivotal mounting dimensioned and configured to permit movement of the first and second generally planar wings to a position wherein the first and second generally planar wings are disposed in parallel overlapping relationship. The cartridge may have the first and second generally planar wings dimensioned and configured for passage within a slot within the associated neuromonitoring needle electrode placement gun. The first and second generally planar wings carried on the housing by a pivotal mounting dimensioned and configured to permit movement thereof to a position wherein the first and second generally planar wings may be disposed in parallel overlapping relationship and the wings shield the respective pointed axial extremities to prevent either intentional or inadvertent contact with the respective pointed axial extremity of each of the elongated needle electrodes.

The cartridge may have the first and second generally planar wings carried on the housing by a pivotal mounting dimensioned and configured to permit movement of the first and second generally planar wings to a position wherein the first and second generally planar wings are disposed in parallel overlapping relationship. The cartridge may have the first and second generally planar wings dimensioned and configured for passage within a slot within the associated neuromonitoring needle electrode placement gun. The first and second generally planar wings carried on the housing by a pivotal mounting dimensioned and configured to permit movement thereof to a position wherein the first and second generally planar wings may be disposed in parallel overlapping relationship and the wings shield the respective pointed axial extremities to prevent either intentional or inadvertent contact with the respective pointed axial extremity of each of the elongated needle electrodes.

The first and second generally planar wings carried on the housing are movable to a position wherein the first and second generally planar wings are substantially coplanar in some embodiments and one side of each of the first and second generally planar wings may be coated with a releasable adhesive suitable for simultaneous engagement with the skin of an associated patient.

The invention also includes a neuromonitoring needle electrode placement gun which includes a housing; at least a first needle electrode and housing assembly; an elongated channel dimensioned and configured for accommodating axial movement of the at least a first needle electrode and housing assembly within the channel and for directing movement of the at least a first needle electrode and housing assembly; and a pusher dimensioned and configured for engaging the at least a first needle electrode and housing assembly and for axially displacing the at least a first needle electrode and housing assembly.

In some embodiments the gun further includes a plurality of needle electrode and housing assemblies disposed in the channel. In some embodiments of the gun each needle electrode and housing assembly includes a needle electrode having a free end and a second end engaging the housing. The neuromonitoring needle electrode placement gun may have a discharge axial extremity and each needle electrode and housing assembly is oriented in the channel with the free end of each needle electrode facing the discharge axial extremity.

The neuromonitoring needle electrode placement gun in some embodiments may have a needle electrode and housing assembly that includes a cartridge for cooperation with an associated neuromonitoring needle electrode placement gun which includes a housing; at least one elongated needle electrode having an axial extent and having a pointed axial extremity carried by the housing; and at least a first generally planar wing having first and second faces thereof, the first generally planar wing being carried by the housing.

The neuromonitoring needle electrode placement gun in some embodiments may have a needle electrode and housing assembly that includes a cartridge for cooperation with an associated neuromonitoring needle electrode placement gun which includes a housing; at least one elongated needle electrode having an axial extent and having a pointed axial extremity carried by the housing; and at least a first generally planar wing having first and second faces thereof, the first generally planar wing being carried by the housing.

Each cartridge may include at least a first generally planar wing that is coated with a releasable adhesive on the first face thereof and each cartridge may have engagement surfaces disposed on opposed sides thereof, the engagement surfaces being dimensioned and configured for cooperation with the elongated channel. In addition, each cartridge may further include an electrically conducting wire fixed to the at least one needle electrode for conducting either a stimulus for a patient or a patient's response to a stimulus. In addition the at least one needle electrode may have insulation surrounding an axial portion of the axial extent of the at least one elongated needle electrode. In addition the insulation surrounding an axial portion of the axial extent of the at least one elongated needle electrode may be spaced a predetermined distance from the pointed axial extremity whereby more precise results are achieved.

Each cartridge may further include a second elongated needle electrode having an axial extent and having a pointed axial extremity carried by the housing. The free ends of each needle electrode in each cartridge may point in the same direction and the first and second elongated needle electrodes may be disposed in coplanar relationship and the first and second elongated needle electrodes in any cartridge may have the respective pointed axial extremities thereof disposed in perpendicular relationship to and abutting a virtual line that is coplanar with the first and second elongated needle electrodes.

The first and second elongated needle electrodes in any cartridge may be spaced apart. Each neuromonitoring needle electrode placement gun may have a cartridge that includes a second generally planar wing having first and second faces thereof, the second generally planar wing being carried by the housing. The first and second generally planar wings are carried on the housing by a pivotal mounting dimensioned and configured to permit movement of the first and second generally planar wings to a position wherein the first and second generally planar wings are disposed in parallel overlapping relationship.

The first and second generally planar wings may be dimensioned and configured for passage within the elongated channel. The first and second generally planar wings may be carried on the housing by a pivotal mounting dimensioned and configured to permit movement thereof to a position wherein the first and second generally planar wings are disposed in parallel overlapping relationship and the wings shield the respective pointed axial extremities to prevent either intentional or inadvertent contact with the respective pointed axial extremity of each of the elongated needle electrodes.

The first and second generally planar wings carried on the housing may be movable to a position wherein the first and second generally planar wings have planar surfaces thereof moveable to a position where the planar surfaces are in abutting relationship. In some embodiments one side of each of the first and second generally planar wings is coated with a releasable adhesive suitable for simultaneous engagement with the skin of an associated patient.

BRIEF DESCRIPTION OF THE DRAWINGS

The subject matter which is regarded as the invention is particularly pointed out and distinctly claimed in the concluding portion of the specification. The invention, however, both as to organization and method of practice, together with the further objects and advantages thereof, may best be understood by reference to the following description taken in connection with the accompanying drawings in which:

FIG. 6C is a side view of pivotally mounted "wings" that are attached to the needle and wire block assembly shown in FIG. 5.

FIG. 6A and FIG. 6B are enlarged section details of the apparatus shown in FIG. 6C illustrating respectively the spring actuated rotation of the top wing and spring loading of the top wing.

DETAILED DESCRIPTION

While the invention has been described in detail herein in accordance with certain preferred embodiments thereof, many modifications and changes therein may be effected by those skilled in the art. Accordingly, it is intended by the appended claims to cover all such modifications and changes as fall within the spirit and scope of the invention.

Figure 3:
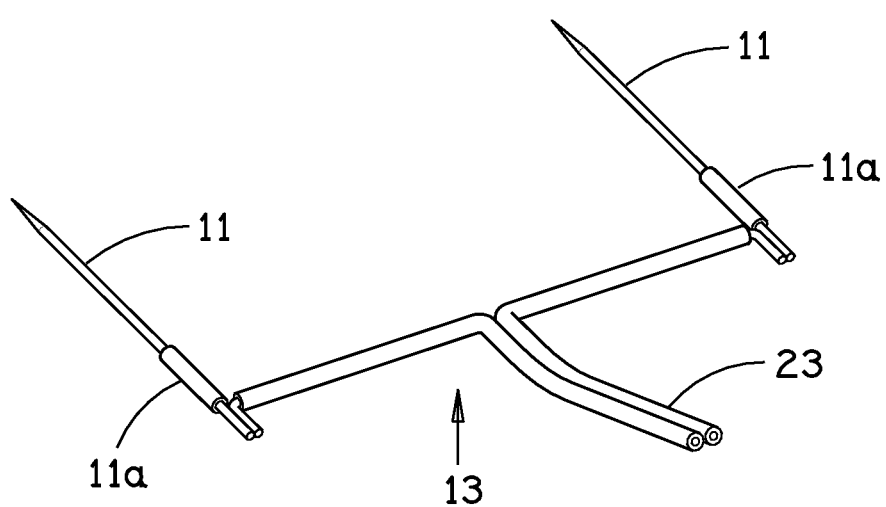
FIG. 3 is a perspective view of an embodiment of a needle and wire assembly that is incorporated into another assembly and then utilized with gun assembly shown in FIG. 1.
Figure 4:
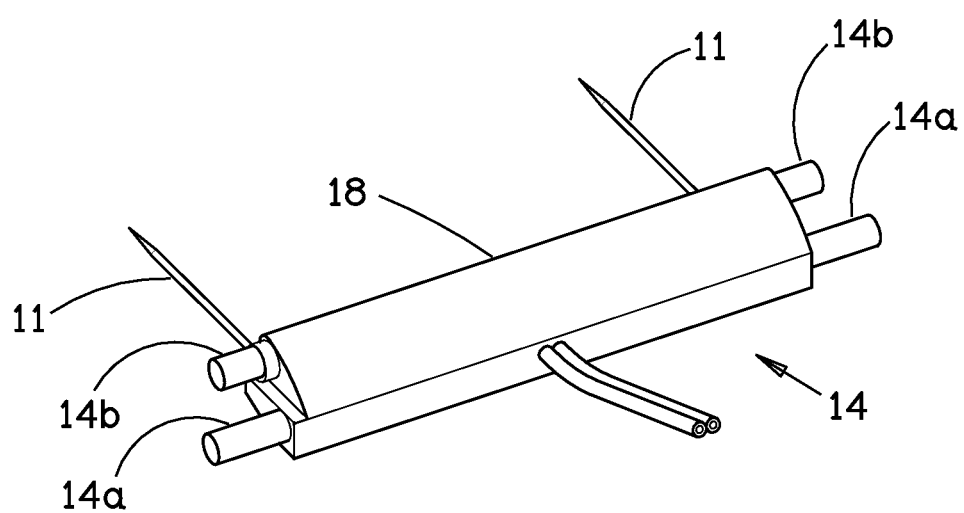
FIG. 4 is a perspective view of an embodiment of the needle and wire assembly shown in FIG. 3 to which a needle block has been molded resulting in a needle and wire block assembly.
Figure 5:
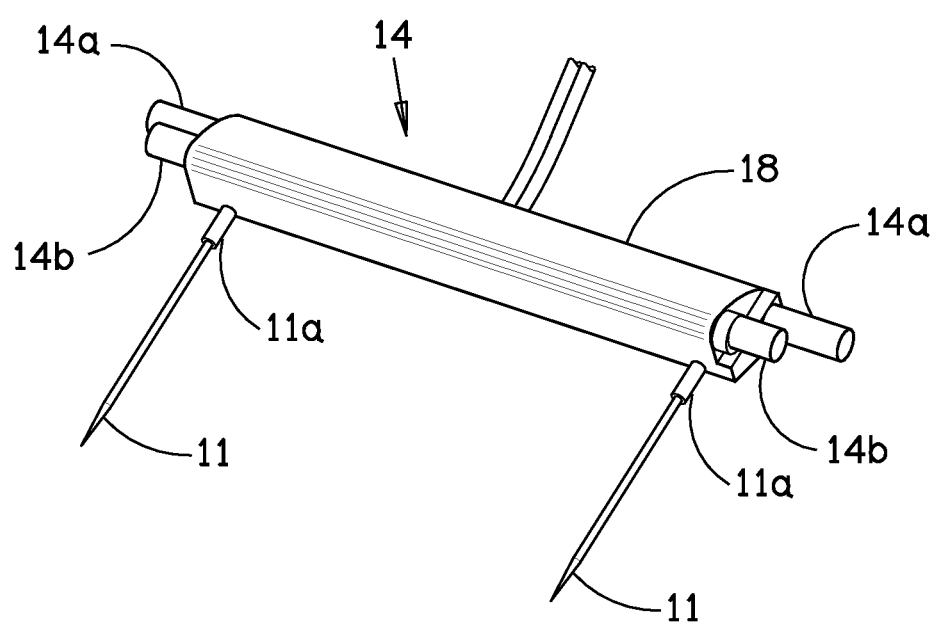
FIG. 5 is another perspective view of the embodiment illustrated in FIG. 4.

The apparatus and method for applying neuromonitoring needles to a patient and the means to connect to monitoring equipment are shown in FIGS. 1-30. The present invention provides a neuromonitoring needle-cartridge gun 10 having a handle 10a and a body 10b best shown in FIGS. 1-2. The gun 10 cooperates with respective twin needle and wire block assemblies 16. Each twin needle and wire block assembly 16 comprises a twin needle assembly 13 with insulated wire pair 23 and connectors 13a as shown in FIG. 3 and FIG. 2 respectively, which further includes a molded block 18 extending over a part thereof as shown in FIG. 4.

The respective needles 11 in a twin needle and wire block assembly 16 are propelled into the patient with a single trigger 22 pull. In a preferred embodiment, it makes no difference if the operator holds or releases the trigger 22 after making an initial trigger 22 pull. After securing the needles 11 (and thereby twin needle and wire block assembly 16 to the patient, the gun 10 is withdrawn, whereupon a coiled extension 24 of insulated wire pair 23 with connectors 13a is extended from a wire cassette 26.

Figure 2:
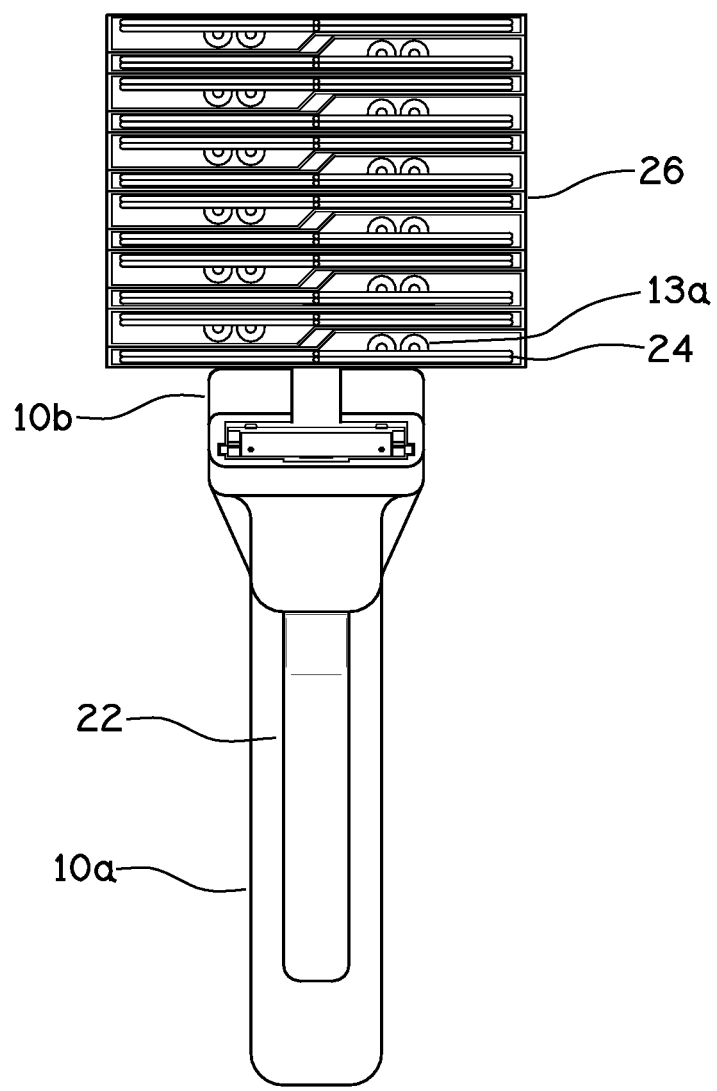
FIG. 2 is a front view of the assembly shown in FIG. 1.

FIG. 2 shows the gun 10 from a front view. The gun 10 is loaded with twin needle and wire block assembly 16 and their associated coil of twin-lead wire 24, with connectors. Each coil of twin-lead wire 24 has enough wire to travel from the needle 11 placement in the patient to the monitoring equipment (not shown), where the connectors 13a are attached after placement of the respective needles in the patient. The coils of twin-lead wire 24 are stacked in a cassette 26. The cassette 26 has a plurality of parallel shelves 28. The cassette has an open front whereby respective coiled extension 24 of insulated wire pair 23 are respectively dragged out of the cassette 26 after a trigger 22 pull as the gun 10 is moved away from the patient.

Respective coiled extensions 24 of insulated wire pairs 23 with connectors 13a are stratified in an orderly manner, so that the top coiled extension 24 of insulated wire pair 23 with connectors 13a comes out of the cassette 26 first followed sequentially by the next highest coiled extension 24 of an insulated wire pair 23. Thus, there is no crossing or tangling of wires. The view of FIG. 2 shows twelve wire coils 24 with connectors 13a disposed in the gun 10. The quantity of wire coils may be more or less in various embodiments of the present invention.

Figure 1:
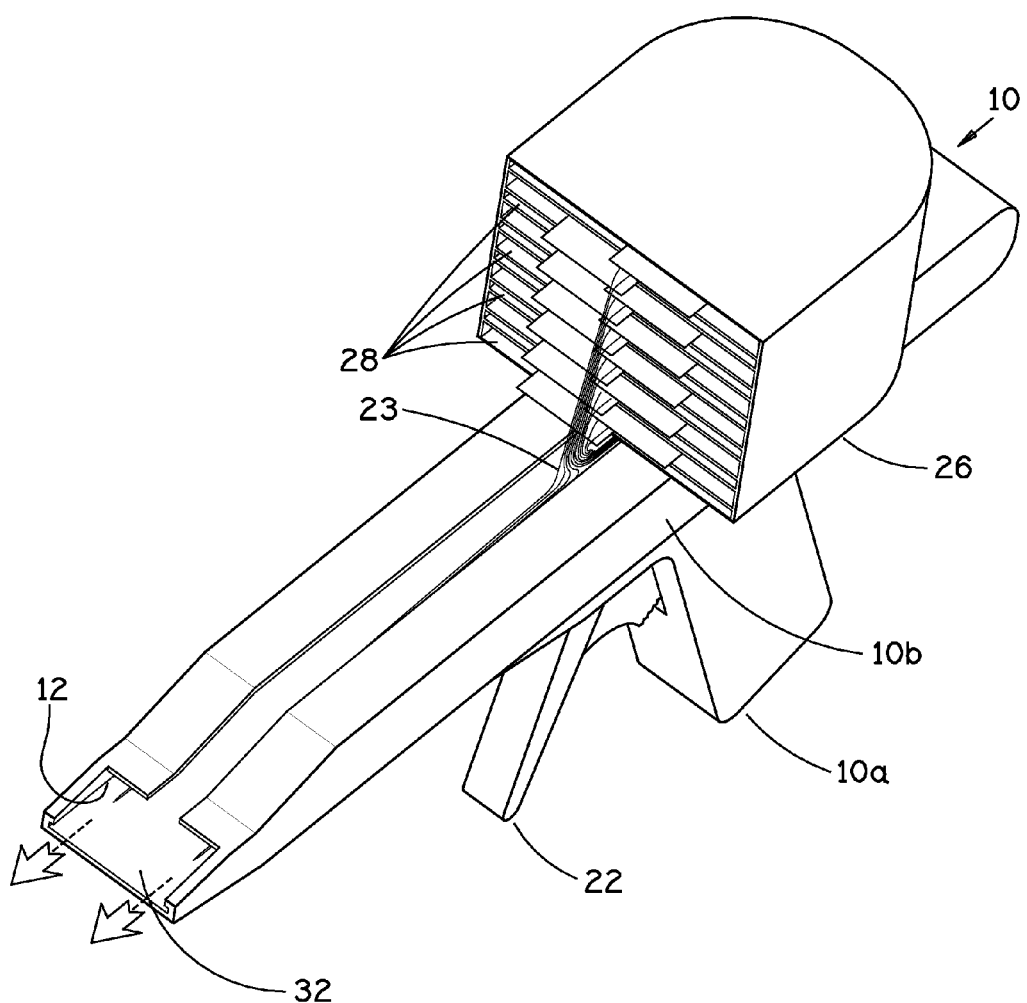
FIG. 1 is a perspective view of an embodiment of a neuromonitoring needle-cartridge gun 10 assembly in accordance with one form of the present invention.
Figure 26:
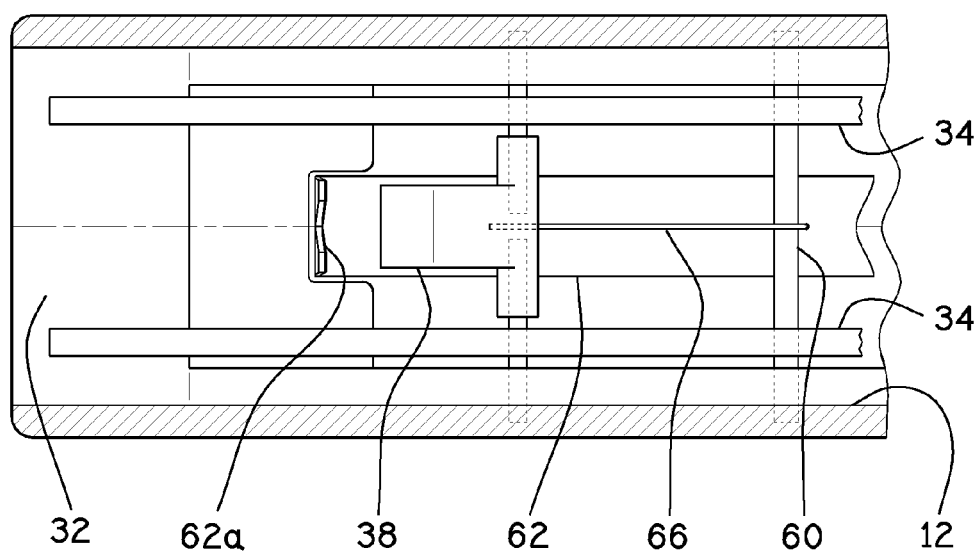
FIGS. 26 and 27 are respectively vertical and horizontal sectional views of the front end of the gun.
Figure 27:
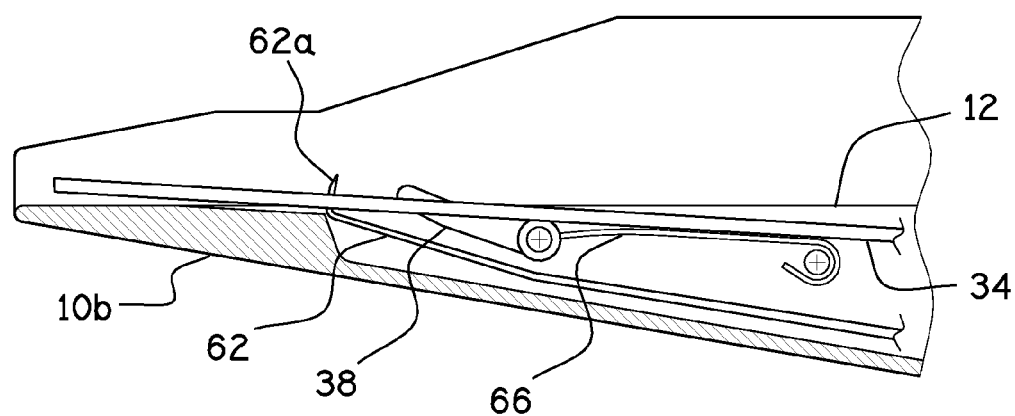

The needles 11 in the gun track 12 are aimed directly out the open end as shown in the left (as viewed) part of FIG. 1 as well as FIGS. 26 and 27. Until the trigger 22 is actuated, the needles 11 are recessed in the track 12. Accordingly, the needles 11 cannot be touched either inadvertently or intentionally. In this embodiment, the cassette shelves 28 have a "zigzag" step in which respective coiled extensions 24 of insulated wire pairs 23 are stacked alternately upside-down and upside-up to conserve space with connectors 13a off to one side. Embodiments of the present invention employ such arrays to lower the overall stack height and thereby result in a lower profile to the overall apparatus. More specifically as shown in FIG. 2, the connectors 13a appear as two side-by-side stacks of twin connectors. Each pair of connectors 13a is attached to a full-width coil of wire 24, and the wire and connector assemblies are stacked alternately, one up, one down. The uppermost coil 24 with connectors 13a is connected to the front-most needle and wire assembly 14 on the needle output deck 32 of the gun 10. Other embodiments may utilize a community mailbox like set of pigeonholes to receive respective coiled extension 24 of an insulated wire pair 23.

FIG. 3 illustrates the construction of a twin needle assembly 13. Each conductor of an insulated wire pair 23 is permanently joined in electrical contact with a respective needle 11 in a twin needle assembly 13. These two conductors become an insulated wire pair 23 at the midpoint between the needles 11, and extend rearward relative to needle 11 direction as best seen in FIG. 3. Each needle 11 is provided with a tight-fitting insulating sleeve 11a, such as shrink tube, so that insulating sleeve exposes a precise length of the axial extremity of each needle 11a. This is to satisfy requirements of the monitoring equipment for accuracy of nerve impulse measurements.

Figure 7:
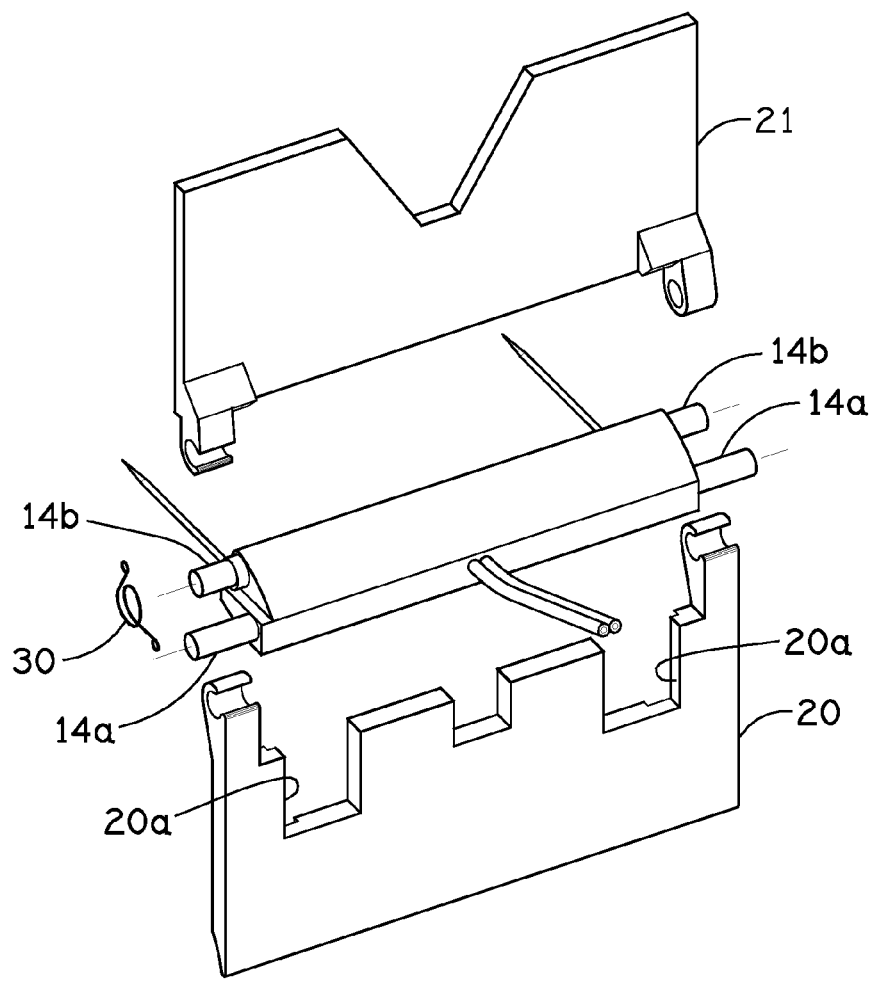
FIG. 7 is an exploded view illustrating a pair of wings that are dimensioned and configured to be snapped onto the needle block assembly.
Figure 8:
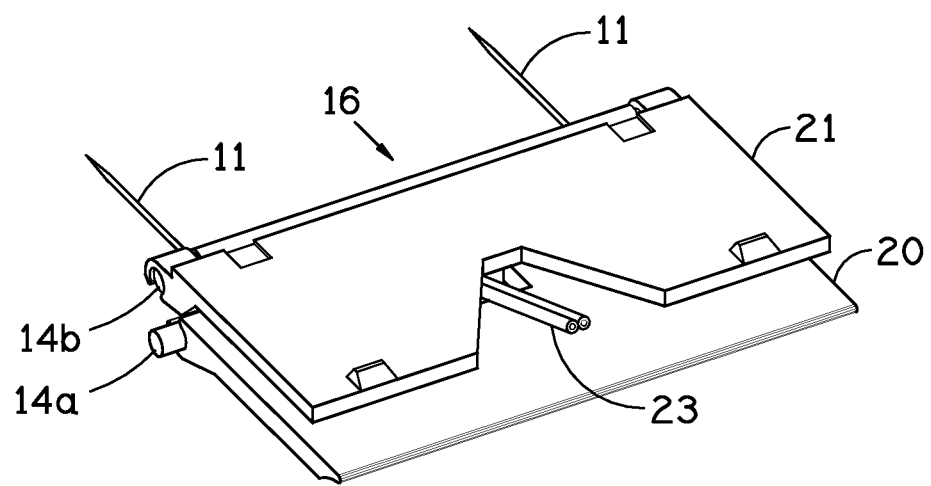
FIG. 8 is another view further illustrating a pair of wings that are both dimensioned and configured to be snapped onto the needle block assembly

The twin needle and wire block assembly 16 consists of a twin needle assembly 13 and a molded block 18. A higher assembly that further includes wings 20 and 21 is shown in FIG. 6C and FIG. 7.

FIG. 4 shows a molded block 18 molded over the needles and the wires. The insulated wires exit the block centrally as a "twin-wire" joined pair (destined for the "wire cassette"). A molded block 18 spans the width of the track 12 in the gun 10, and pivotally supports a bottom wing 20 and a top wing 21 best seen in FIG. 7. The wings 20, 21 secure the assembly to the patient.

FIGS. 6A, 6B, 6C and FIG. 7 illustrate the relationship of pivotally mounted wings 20, 21 to the molded block 18. The upper or top wing 21 is spring loaded by a little low force wire-form spring 30 placed inboard on the pivot pin prior to snapping on the wing 21. This spring 30 urges the upper wing 21 to swing up to its initial installed vertical position as shown in FIG. 6A. This movement of the upper wing 21 in response to the bias of the spring 30 occurs after the needle assembly 14 is propelled to the output deck 32 of the gun 10 in the customary use of the illustrated embodiment of the present invention. The respective pairs of wings 20, 21 are respectively snapped on coaxial bottom pins 14a and coaxial upper pins 14b carried by the molded block 18. The upper wing 21 retains the spring 30, as noted above. The spring 30 cannot escape from its installed position due to the loops at each end (best seen in FIGS. 6A and 6B), which will not fit through the cracks of the structure. Coaxial bottom pins 14a disposed at the opposed axial extremities of the molded block 18 extend out beyond coaxial upper pins 14b also disposed at the opposed axial extremities of the molded block 18. The coaxial bottom pins 14a ride in grooves on opposed sides of the gun track 12 in order to provide further guidance for the needle and wire assembly 14 as it advances along the track 12 in the gun 10.

The two-spaced rectangular open-ended cutouts 20a (shown in FIG. 7) in the lower wing 20, provide clearance for the pusher rails 34 to extend behind a needle and wire block assembly 16 that is next to be pushed. See FIGS. 15A, 15B, 16A, and 16B.

The wings 20, 21 each have an adhesive coating, protected from exposure until use, by a layer of release paper that is easily pulled off by the operator at the time of application to the patient. The top wing 21 has the adhesive on the broad flat top surface thereof and the bottom wing 20 has the adhesive on the broad flat bottom surface thereof. The operator exposes the adhesive on the pivotally mounted wings 20, 21 and presses the respective adhesive surfaces thereof to the skin of the patient being monitored and thereby secures the assembly to the patient.

A preferred embodiment described herein contains 12 needle assemblies lined-up in the gun track 12, and corresponding 12 sets of wires including connectors 13a, tucked in a stratified manner into the wire cassette above the track 12. The needle assemblies are lined-up nose-to-tail, not counting the needles, which ride below the wing 20 of the preceding assembly.

Figure 9:
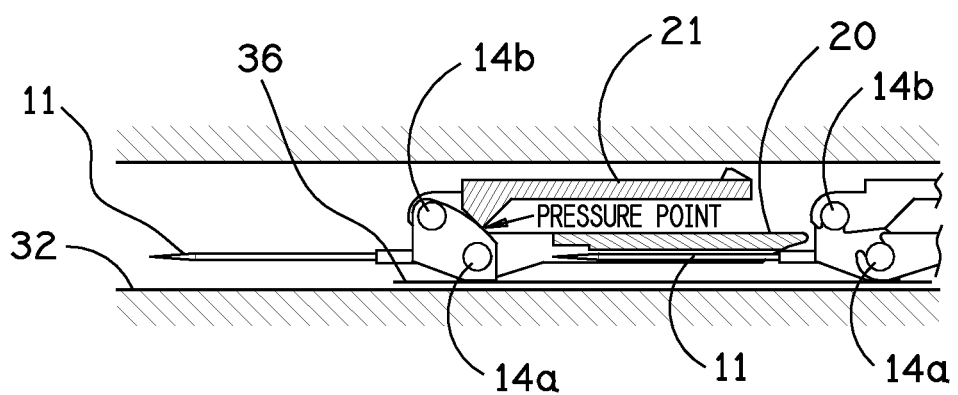
FIG. 9 is a partially schematic and section view illustrating the construction of an embodiment in which the needles are secured within the gun in a manner that precludes any touching of the needles after loading the needles into the gun and immediately prior to placement in a patient.

As best seen in FIG. 9 the points of the needles 11 do not touch anything at any time prior to subcutaneous placement in a patient. The needles cannot drop to the track 12 floor because the roof of the gun track 12 holds down the upper wing 21, and that wing 21 bears against the needle and wire block assembly 16 and thus prevents the needle and wire block assembly 16 from rotating downward with the needle 11.

Figure 10:
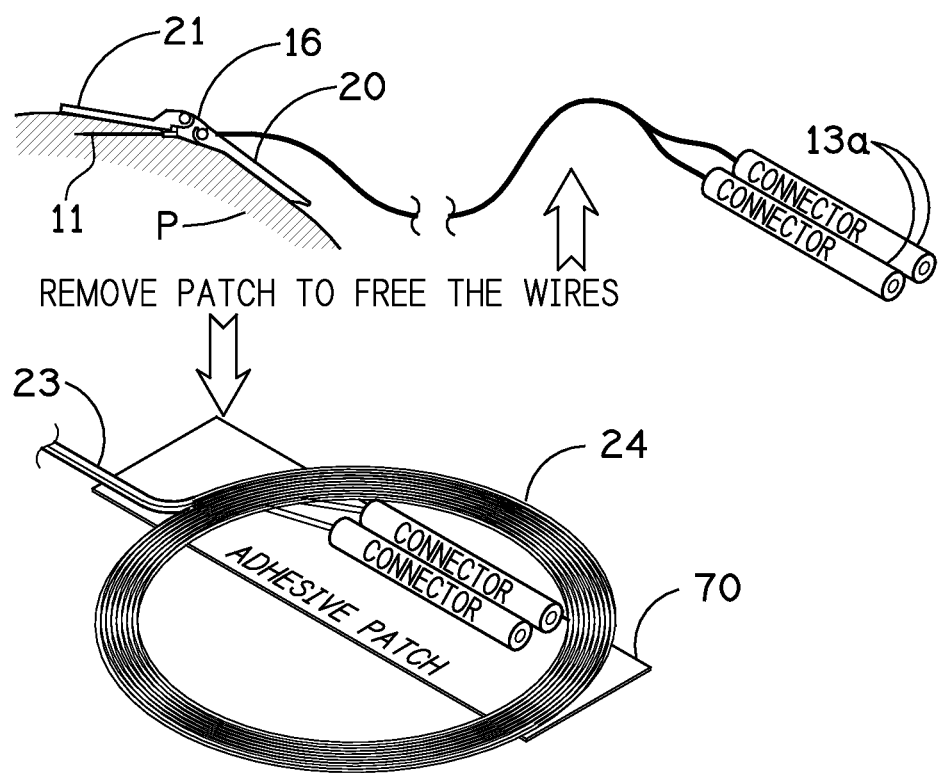
FIG. 10 is a partially schematic view of a connection between a wire coil, with connectors, and the needle assembly that is adhered to the patient.

As best seen in FIG. 10 the coil of twin-lead wire 24 is connected by connectors 13a to a needle and wire block assembly 16 that is adhered to the patient P. The wire coil 24, with its connectors, is dragged from one of the respective shelves 28 in the cassette 26. The coil 24 includes a long free wire upon pulling the coiled extension 24 of insulated wire pair 23 away from a relatively low tack adhesive patch 70 that initially secures the coiled extension 24 of insulated wire pair 23 to one of the shelves 28 in the cassette 26. Some of the low tack adhesive patch 70 is made to stick to one of the shelves 28 and will release upon the coiled extension 24 of insulated wire pair 23 being dragged as the gun is moved away from the patient P. The main body of adhesive faces the coil 24, and holds it neatly coiled until the operator manually removes the low tack adhesive patch 70 from the coiled extension 24 of insulated wire pair 23. Then the full length of the previously coiled extension 24 of insulated wire pair falls free, ready to be drawn over to the monitoring equipment. This can be done whenever the operator is ready, even after all needles are attached to the patient, and the patient is positioned as desired. The gun track 12 of the gun 10 is elongated. The other axial extremity of the coiled extension 24 of insulated wire pair 23 is fixed to the insulated wire pair 23 that is dimensioned to allow free movement of the needles 11 through the track 12.

Figure 11:
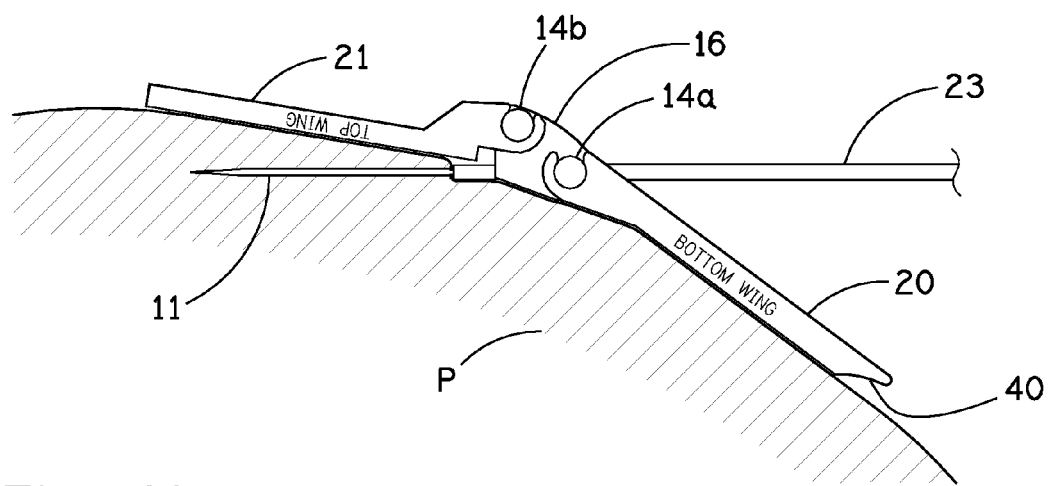
FIG. 11 is an enlarged side view of the needle assembly, shown in FIG. 10, applied to a patient.

FIG. 11 is an enlarged view of the needle and wire block assembly 16 applied to a patient. The angle of entry for the needles is determined by the operator aiming the gun 10. The mounting of the wings 20, 21 permits angular travel to any desired angular orientation about the respective mounting axis thereof and thus the adhesive surfaces thereof can be applied to the skin of the patient. The wings 20, 21 are designed for ease of removing the assembly from the patient.

A fingernail tab 40 assists in lifting the bottom wing 20 from the patient. The rest of the assembly is stripped from the patient by pulling the upper wing 21 and the wire. The insulated wire pair 23 in a preferred embodiment is ruggedized and securely mounted in the needle and wire block assembly 16.

Figure 12:
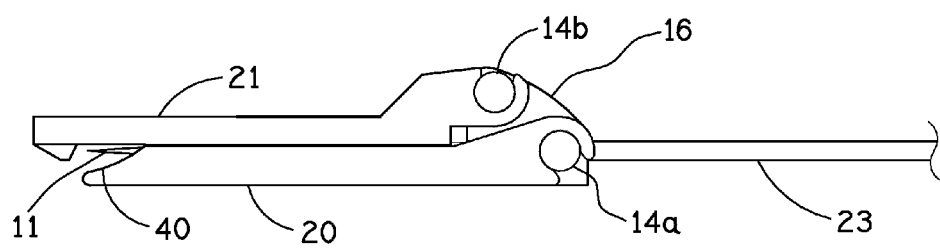
FIG. 12 shows the needle assembly after removal from the patient.

FIG. 12 shows the needle and wire block assembly 16 after removal from the patient. The wings 20, 21 are disposed in planar face to planar face contact. The respective planar faces immediately stick to each other because they still have the adhesive that stuck to the skin of the patient. The needles 11 are obscured between the wings 20 and 21, and thus protected from both intentional and unintentional contact by anybody. Post-operative cleanup is now much safer than in prior art manual procedures because there are no exposed needles 11. The rugged insulated wire pair 23 functions as a lanyard that can be pulled as needed during removal.

Figure 13:
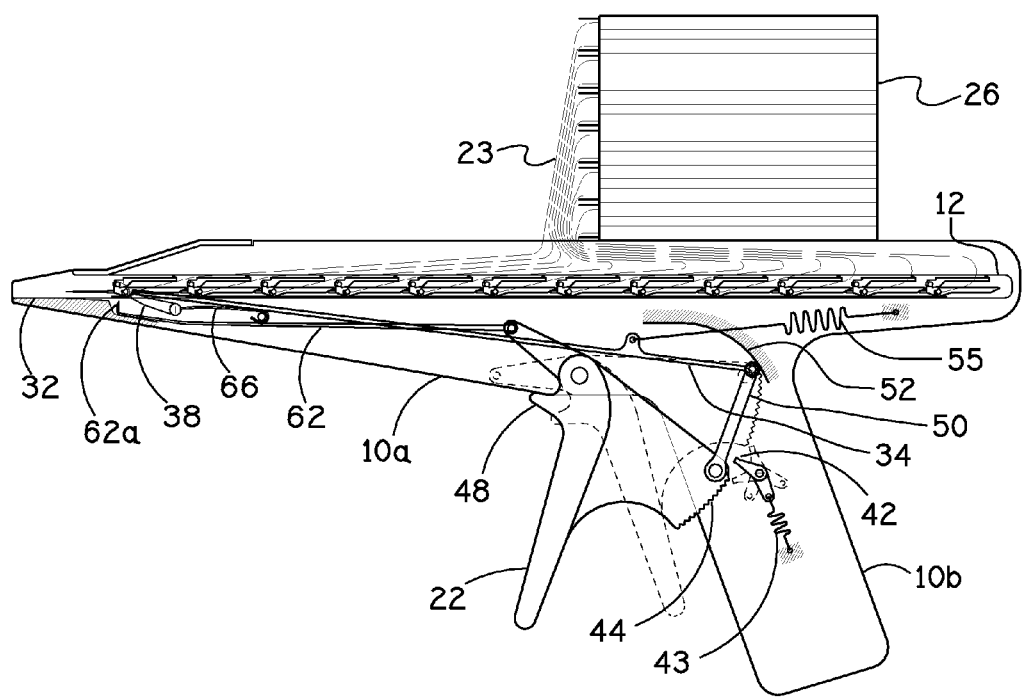
FIG. 13 is a partially broken-away side view of the overall gun 10, fully loaded with a plurality of needle and wire block assemblies that are ready to fire for subdermal implant of the axial extremities of the respective needles in a patient.
Figure 28:
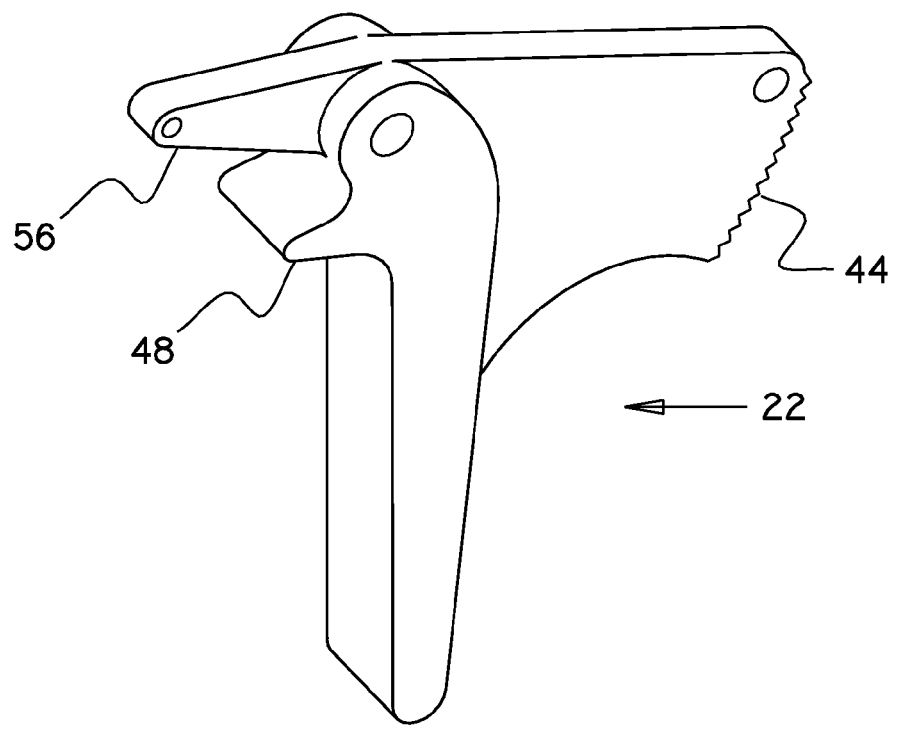
FIGS. 28 and 29 are isometric views of one embodiment of the trigger.
Figure 29:
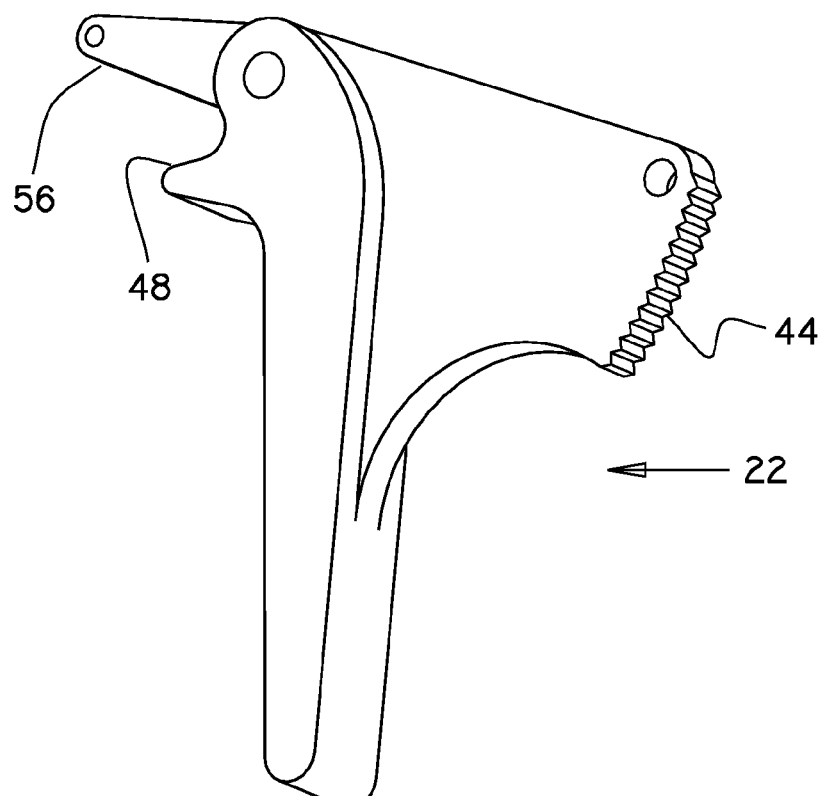

FIG. 13 is a partially cut-away side view of the overall gun 10, fully loaded and ready to fire. The trigger 22, also shown in FIGS. 28, 29 is a lever, which can be operated by one or more fingers. A bi-directional anti-backup trigger pawl 42 engages a rotary ratchet 44 on the rear of the trigger 22 after the trigger 22 has been moved a short distance from the initial position. It will be understood that the rotary ratchet 44 formed on a planar member is rigidly fixed to the trigger 22 and thus has the same center of rotation as the trigger 22. (In some embodiments, the rotary ratchet 44 and the rest of the trigger 22 are manufactured from a single piece and that piece is metal.) Because of the bi-directional anti-backup trigger pawl 42 engagement with the rotary ratchet 44 on the rear of the trigger 22 the trigger 22 must be fully actuated before the trigger 22 can reset back to the initial position. The trigger pawl 42 also works in the other direction, so that once the trigger has moved away from the handle 10a, the trigger 22 must return to the initial position where the trigger is spaced from the handle the maximum possible distance before another firing cycle can occur. A trigger pawl spring 43 pulls the spring-loaded bi-directional pawl 42 to its central waiting or default position. In addition, the trigger 22 has motion limit stop 48 to preclude overtravel.

Figure 14:
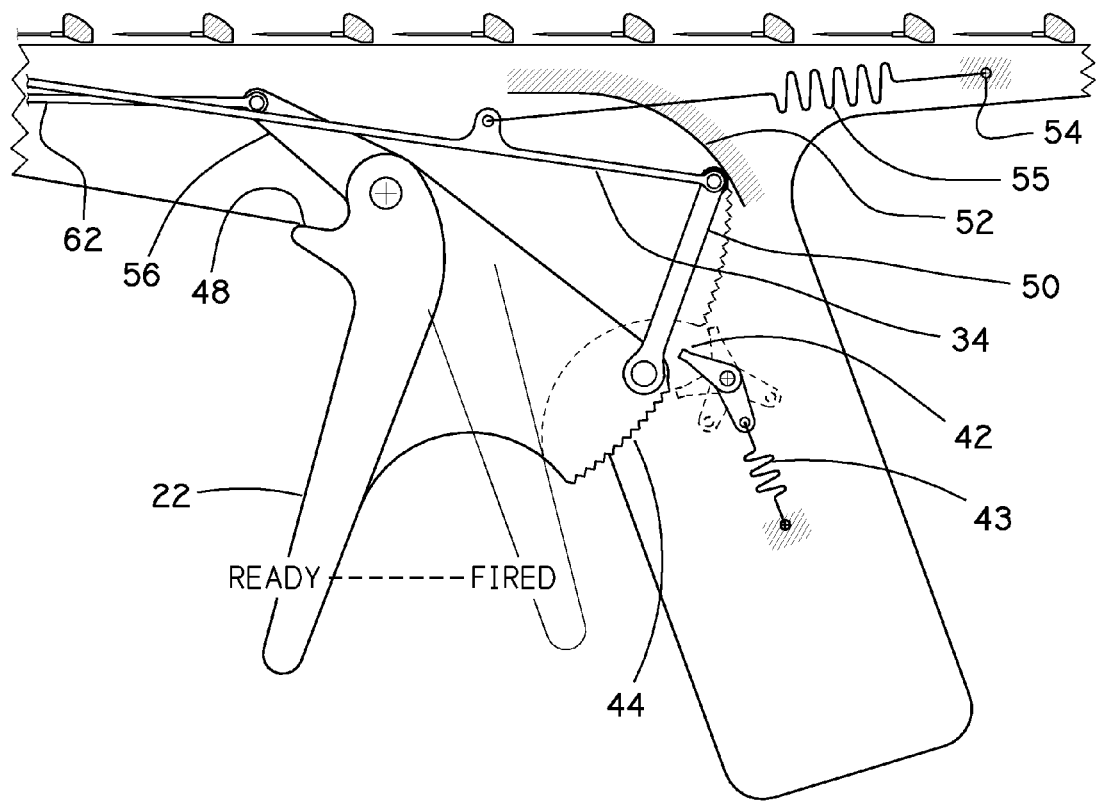
FIG. 14 is an enlarged partially schematic view of the trigger area of the apparatus shown in FIG. 13.

FIG. 14 is a view of the trigger 22 area of the FIG. 13. Also shown are simplified views of parts needle and wire block assembly 16 (just needles and needle blocks) to illustrate how the needles 11 ride in the gun track 12 including illustrating how the points of the respective needles 11 travel without interference. The respective legs of the pusher rail 34 are propelled forward when the trigger 22 is actuated. More particularly the pusher rail 34 is propelled by an elongated link 50 riding on an arcuate cam ramp 52. Return force for combined pusher rail 34, elongated link 50 and trigger 22 is provided by a trigger return spring 55 connecting the pusher rail 34 to a fixed point 54 on the gun 10. The trigger return spring 55 is disposed in a different plane than the arcuate cam ramp 52 to avoid interference. The trigger return spring 55 also provides an upward force for the pusher rail 34, so that the pusher rail 34 will snap in behind the next-in-line needle and wire block assembly 16, upon trigger 22 return (reset) to the initial position as shown in FIG. 13. The horizontal travel of the forward arm 56 of the trigger 22, which drives the ribbon-parting blade 62 is non-linear, and stays at nearly the same horizontal location for the last half of the trigger actuation so the parting blade remains where needed. This positions the blade for ribbon parting synchronized with the pusher displacement. The blade is cammed up with appropriate timing, as seen later in FIGS. 19-24.

Figure 15A:
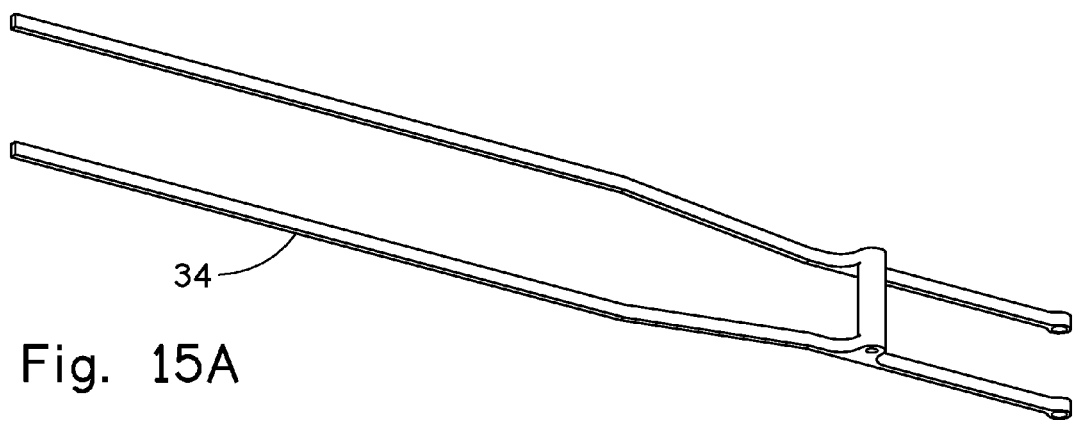
FIG. 15A is a perspective view of a twin pusher element of the gun 10 constructed to positively urge each of the respective needles in a given needle assembly for subdermal implant of the axial extremities of the respective needles in a patient.
Figure 15B:
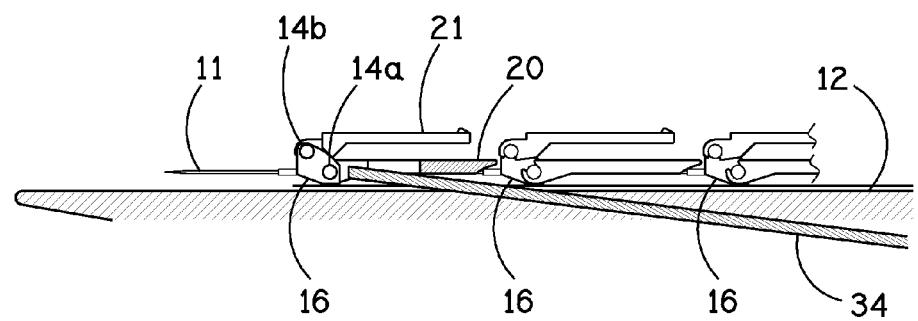
FIG. 15B is a partially schematic view illustrating the manner of engagement between the twin pusher element illustrated in FIG. 15A and a given needle block immediately prior to subdermal implant of the axial extremities of the respective needles in a patient.

FIG. 15 shows the pusher rail 34 comprising first and second parallel elongated legs. Each leg of the pusher rail 34 extends through one of open-ended cutouts 20a of the bottom wing 20 to engage a needle and wire block assembly 16. The spaced legs of the pusher rail 34 simultaneously engage spaced apart lateral portions of the needle and wire block assembly 16. This arrangement insures stability of the needle and wire block assembly. FIG. 15B is a side cut-away view showing the pusher rails back at the home position, ready to propel the next-in-line needle and wire block assembly 16 each carrying a respective bottom wing 20 and top wing 21. The push of the pusher rail 34 implants the needles 11 subcutaneously in the patient as best seen in FIG. 17.

Figures 16A, 16B:
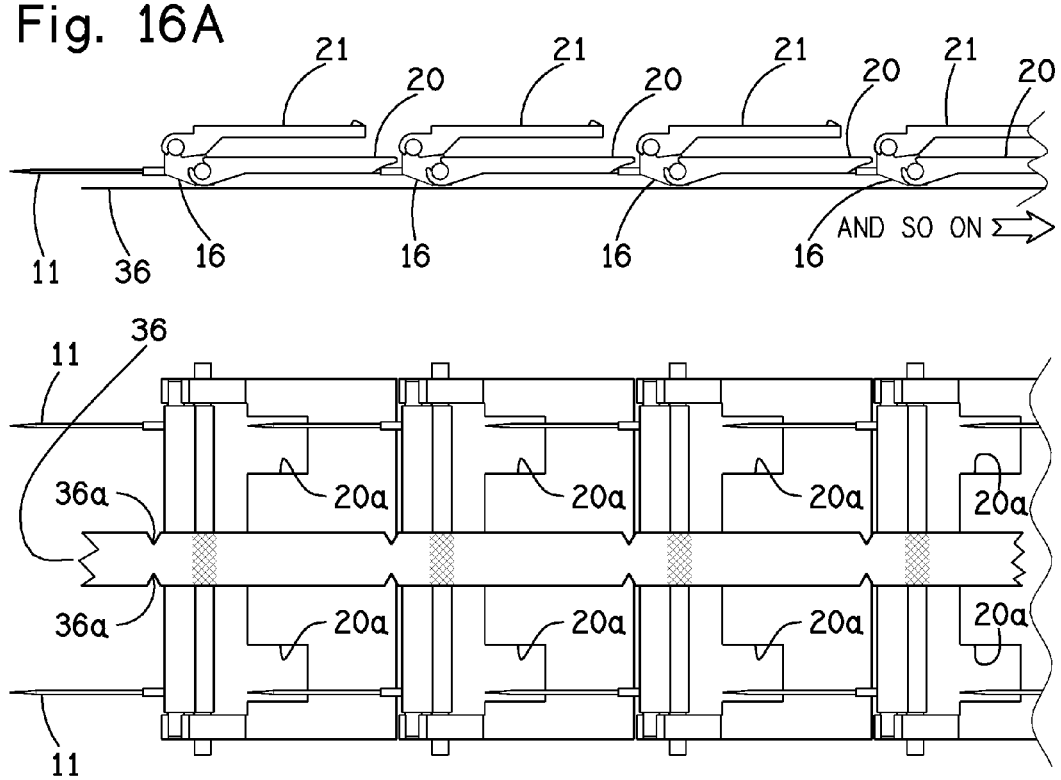
FIG. 16A and FIG. 16B are respectively side and bottom views of an axial part of a column of needle assemblies each carrying a respective bottom wing 20 and top wing 21 permanently joined onto a ribbon that sequentially advances respective needle assemblies.

FIGS. 16A and 16B respectively illustrate a side view and a bottom view of an axial part of a column of needle and wire block assembly 16 carrying a bottom wing 20 and a top wing 21 each joined to a ribbon 36. The distance between identical points on each of two successive needle and wire block assembly 16 is the pitch of the column. The entire column moves one pitch length forward in the gun track 12 when the trigger 22 is cycled between an initial position (as shown) to a fully depressed position. The legs of the pusher rail 34 on the needle and wire block assembly 16 nearest the discharge axial extremity of the track 12 advances both that individual needle and wire block assembly 16 as well as the ribbon 36 and all the other needle and wire block assemblies 16 (each carrying a respective bottom wing 20 and top wing 21) attached to the ribbon 36. The ribbon 36 is provided with a pair of opposed notches 36a at one pitch length intervals along the axial extent of the ribbon 36. The wing 20 clearance cutout areas 20a, shown in the bottom view, allow the pusher 34 legs to get behind the needle and wire block assembly 16 nearest the discharge end of the track 12 to accurately advance both that needle and wire block assembly 16 with the top and bottom wings secured thereto as well as the trailing ribbon and other attached needle and wire block assemblies 16 with their respective top and bottom wings secured thereto.

Figure 17:
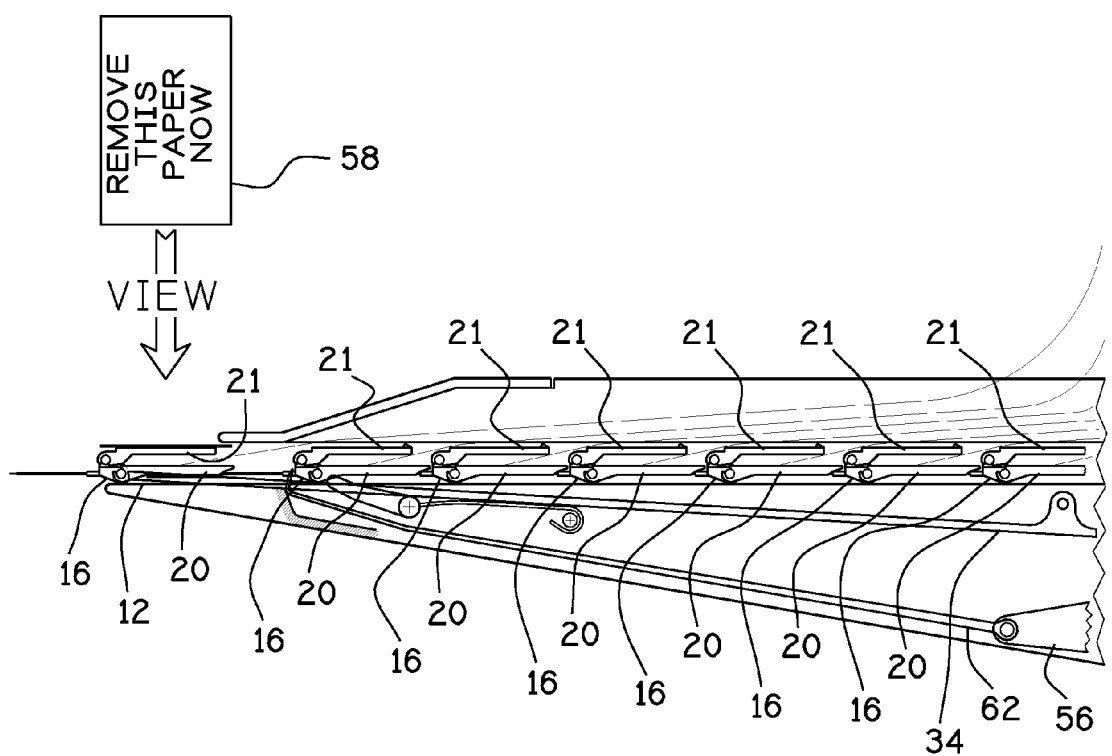
FIG. 17 schematically illustrates the manner in which a needle assembly is propelled fully forward and particularly illustrates a piece of release paper disposed over adhesive disposed on both the top and bottom wings of a respective needle assembly.

FIG. 17 illustrates the position of a needle and wire block assembly 16 propelled fully forward. A message for the gun 10 operator is automatically presented. Each needle assembly comes with a respective piece of release paper extending over the adhesive on each of the top and bottom wings 20 and 21. Each such release paper overlaps the adhesive slightly to make its removal easier. The top release paper has the printed message illustrated in FIG. 17. This message is prominently presented when the needle and wire block assembly 16 is fully propelled as the result of the trigger 22 being fully actuated. Accordingly, the needles 11 have been propelled into the patient (not shown). The release paper 58 extends back under the top of the gun track 12 in order to retain the position of that spring-loaded wing until the release paper in removed. Upon removal of the release paper 58, the spring 30 also shown in FIGS. 6A-6C swings the wing 21 upward as shown in FIG. 18.

Figure 18:
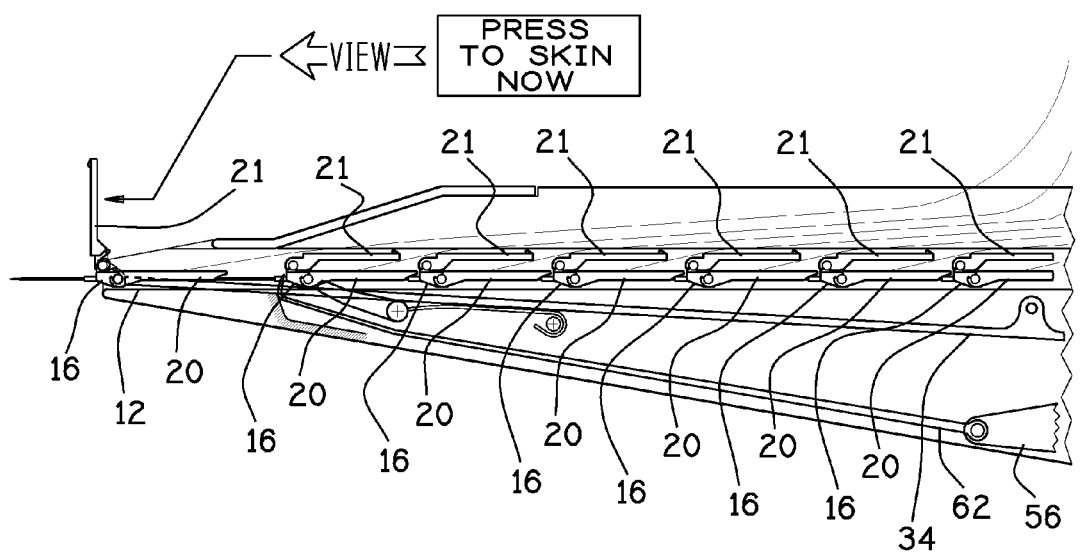
FIG. 18 schematically illustrates the next sequential step in an embodiment of the present invention in which after the axial extremities of the needles are subdermal implanted and removal of the release paper a small spring moves the top wing up to display an instruction to the operator to press the wings against the skin of the patient (to avoid needle sticks) preparatory to withdrawal of gun 10 away from the area of the subdermal implant.

FIG. 18 shows the next step for the operator after the step illustrated in FIG. 17. Upon removing the release paper 58, the spring 30 swings the top wing 21 up to where the next message is prominently displayed. After a respective pair of needles 11 is positioned in the patient (not shown) and the operator presses the wing 21 against the skin of the patient. This secures the needle and wire block assembly 16 to the patient, and the gun 10 is drawn away. As the gun 10 is drawn away, the wire coil 24, with connectors 13*a*, comes out of the cassette 26. The operator removes the release paper 58 from the bottom wing 20 and presses the bottom wing 20 to the skin of the patient. Upon removing the adhesive patch 30 from the wire coil 24 and its connectors 13*a*, a long length of wire is released to deliver the connectors 13*a* to the measurement equipment (not shown).

FIGS. 19-24, show the operation inside the front of the gun 10 during a firing cycle. The ribbon 36, having a plurality of attached needle and wire block assemblies 16 each with an attached top wing 21 and bottom wing 20 is drawn forward. Thereafter, the ribbon 36 is severed so that the then front most needle and wire block assembly 16 each with an attached top wing 21 and bottom wing 20 attached and its associated coiled extension 24 of insulated wire pair 23 can exit the gun 10 while the ribbon with the attachments thereto is held in place. A spring loaded anti-backup pawl 43 is constantly blocking the plurality of needle and wire block assemblies 16 that are collectively referred to herein as a column. More particularly the anti-backup pawl 38 blocks the column from slipping backward. The column has enough friction with respect to the gun track 12 so that the column will resist slipping forward. Upon the occurrence of very unusual circumstances, such as dropping the gun 10 on a hard table surface, the operator will initiate a "clearing" cycle to insure no malfunction has or will occur. This returns the mechanism to a normal condition with everything back to normal, minus one needle and wire block assembly 16 each with an attached top wing 21 and bottom wing 20 attached and its associated coiled extension 24 of insulated wire pair 23. The anti-backup pawl 38 cooperates with a wire-form spring 66 molded into the body thereof at the pivot for the pawl 38. The pawl 38 is biased by the spring 66. The other end of the wire-form spring 66 is fixed on a spring anchor pin 60 carried on the gun body 10*b*.

Figure 19:
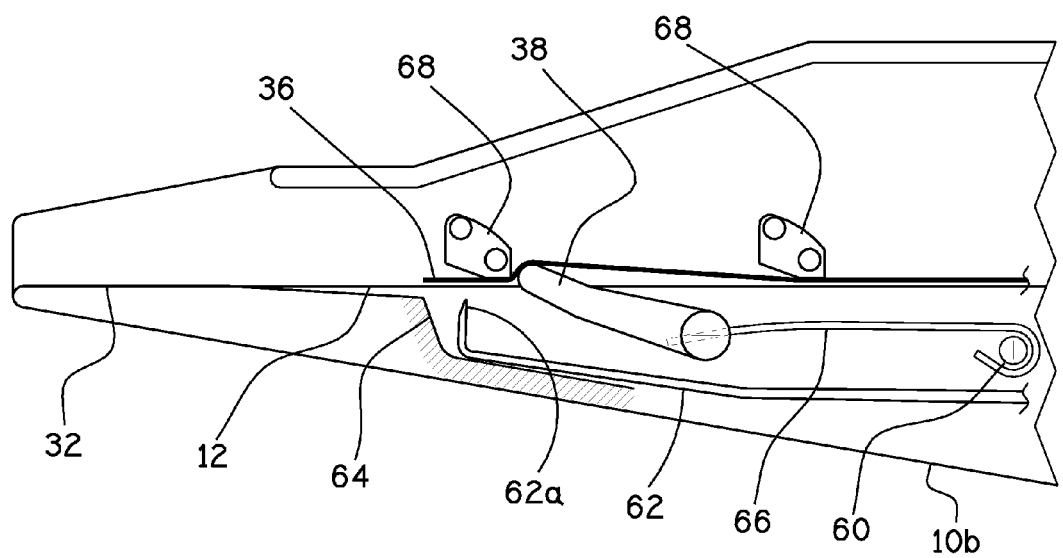
FIG. 19 is a partially schematic representation at an initial position of a part of the gun 10 that is simplified by representing complete needle assemblies by needle blocks to improve clarity.

FIG. 19 shows the condition of a portion of the apparatus before, or at, the start of a firing cycle. For clarity, the view is simplified e.g., blocks 68 represent complete needle and wire block assemblies 16 together with a top wing 21 and a bottom wing 20.

Figure 20:
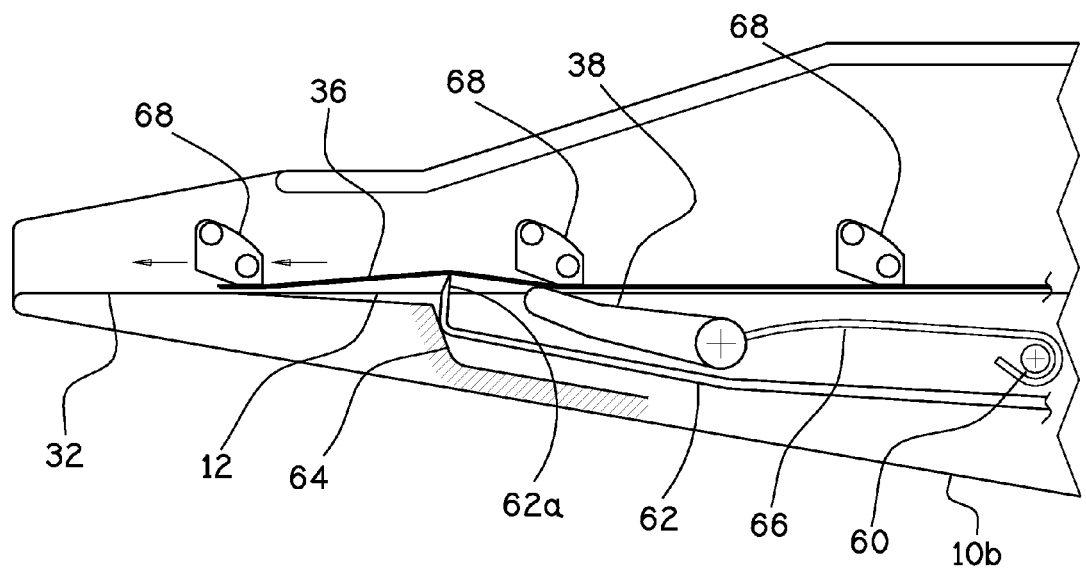
FIG. 20 is a partially schematic simplified representation similar to that shown in FIG. 19 where the needle assemblies are advanced a partial pitch length wherein the term "pitch length" refers to the length between successive needle assemblies.

FIG. 20 shows a plurality of simplified blocks 68 each representing complete needle and wire block assemblies 16 together with a top wing 21 and a bottom wing 20 advanced forward a partial pitch length. The pusher pair (not shown) is bearing on the rear most surface of the leading complete needle and wire block assemblies 16 together with a top wing 21 and a bottom wing 20. The column is advanced forcefully over a pawl 38 (biased by pawl spring 43), which deflects downward. A ribbon-parting blade 62, also shown in FIG. 25 is starting to climb up a ribbon parting blade cam ramp 64. (Cam ramps in this gun 10 are provided with a thin film of silicone grease.) The parting blade 62 in a preferred embodiment is not sharp and does not cut anything. It works on an altogether different principle, illustrated in FIGS. 22, 23 and 24.

Figure 21:
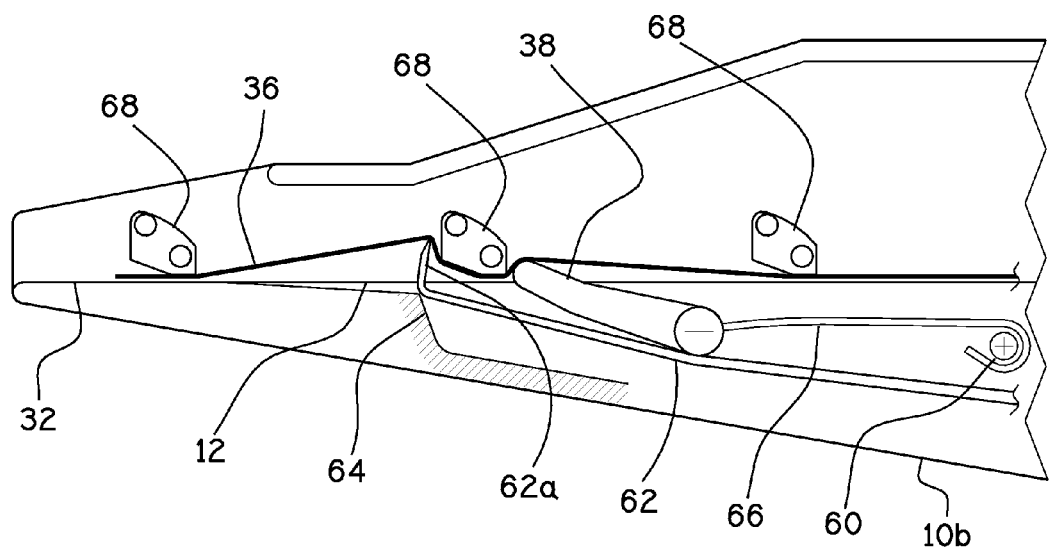
FIG. 21 is a partially schematic simplified representation similar to that shown in FIG. 19 where the needle assemblies are advanced a complete pitch length wherein the term "pitch length" refers to the length between successive needle assemblies.
Figure 22:
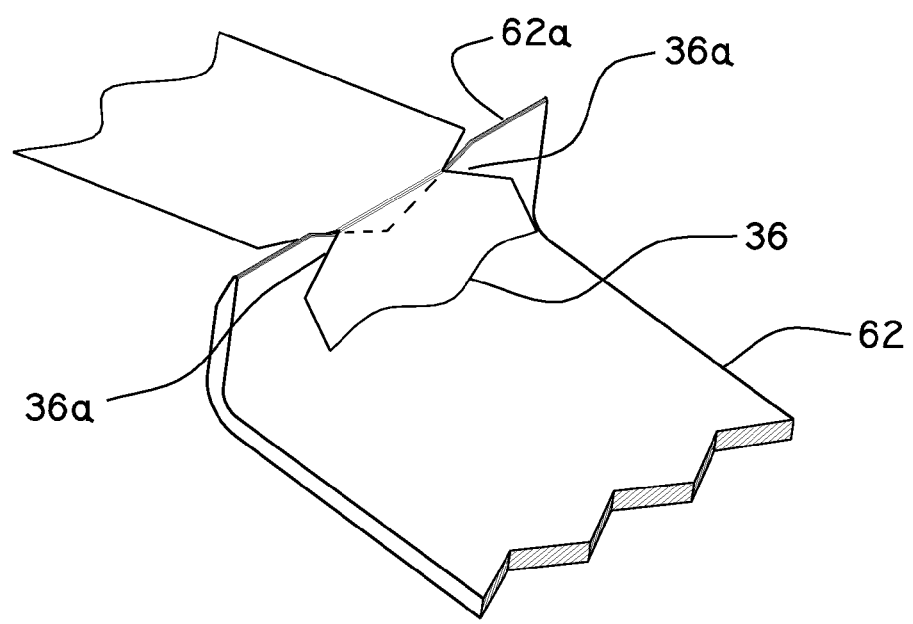
FIG. 22 is a partially schematic representation of the ribbon extending between respective needle assemblies and having respective opposed notches at axially spaced intervals of the ribbon and particularly showing an axial part of the ribbon having opposed notches registered with a parting blade.

FIG. 21 shows blocks 68 representing complete needle and wire block assemblies 16 advanced one full pitch length. The pawl 38 has sprung back up to prevent rearward slippage. The ribbon 36 is attached to the needle and wire block assembly 16 with enough slack to allow the pawl 38 to move far enough upward to, once again, provide positive anti-backup for the train of needle assemblies. The parting blade 62 is cammed to its uppermost position. The ribbon 36 has opposed notches 36*a* at axial intervals equal to the pitch of the mechanism as shown in FIGS. 16B and 22). An engagement surface 62*a* is now registered in the opposed notches 36*a*, each having an acute included angle, with a sharp apex, to facilitate tearing of the ribbon 36. Further motion by the twin pushers (not shown) against the forward needle block starts a tearing action in the ribbon 36 between the opposed notches 36*a*. The next needle block 68 cannot advance forward during the remainder of this cycle because it is up against the rigid parting blade, which will not move.

FIG. 22 shows the ribbon 36 with its opposed notches 36*a* pulled up over the engagement surface 62*a* of a ribbon parting blade 62. The engagement surface 62*a* of a ribbon parting blade 62 is dull, whereas the opposed notches 36*a* of the ribbon 36 have an enclosed acute angle. The next sequential needle and wire block assemblies 16 together with a top wing 21 and a bottom wing 20 with its attached ribbon 36, cannot move any farther because the engagement surface 62*a* of the ribbon parting blade 62 is in the way. Further axial pulling on the ribbon 36 by the forward needle block will cause a tear to start between the opposed notches 36*a* in the ribbon 36. The ribbon 36 tears incrementally as the ribbon parting blade 62 and particularly the engagement surface 62*a* engages the opposed notches 36*a* so there is no sudden pop when the ribbon parts.

Figure 23:
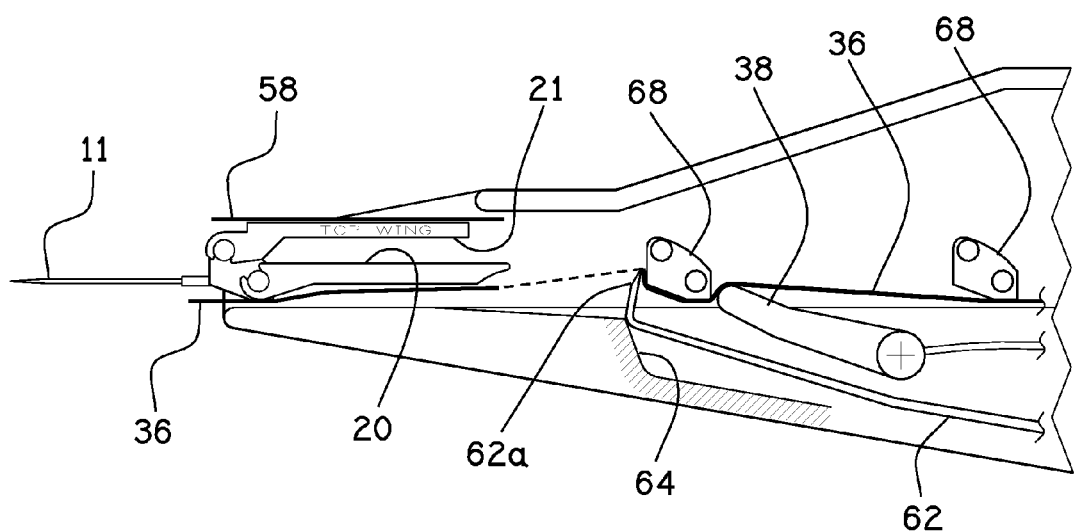
FIG. 23 is a partially schematic simplified representation similar to that shown in FIG. 21 where the needle assemblies are further advanced with the needles in the patient whereby the ribbon is axially moved forward with its needle block concurrently with an axial part of the ribbon having opposed notches registered with a parting blade and thereby initiating a tear in the ribbon at the axial part of the ribbon having opposed notches.

FIG. 23 shows the front needle assembly propelled fully forward. The needles are in the patient (not shown). The ribbon 36 is forced to move forward with its needle block, and therefore forces a tear in the ribbon 36 at the opposed notches 36*a* parts the ribbon 36.

Figure 24:
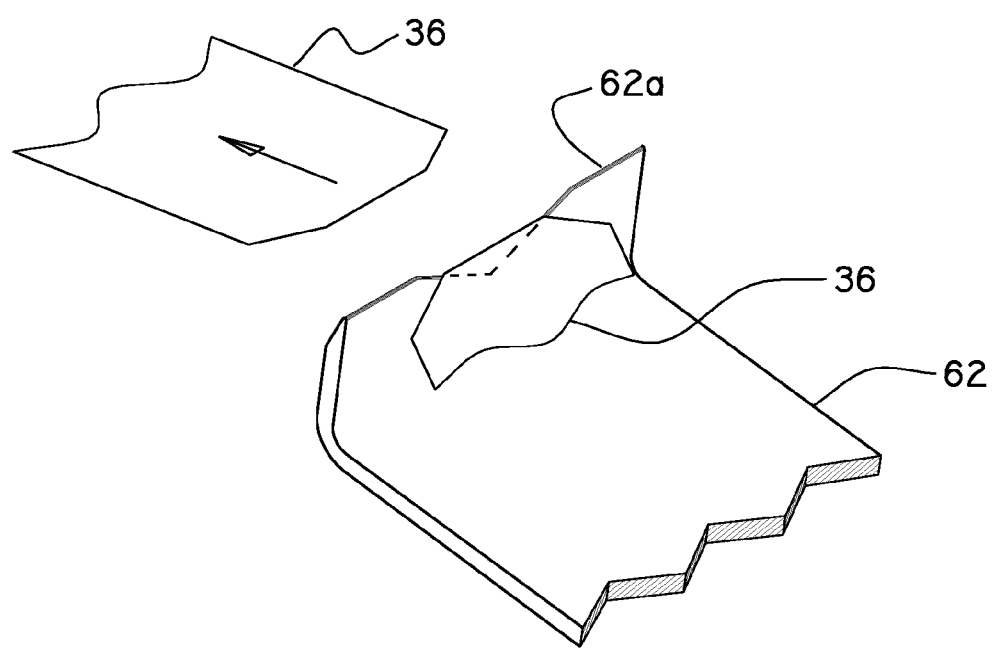
FIG. 24 is a representation of the tearing of the ribbon as a consequence of the movement illustrated in FIG. 23.
Figure 25:
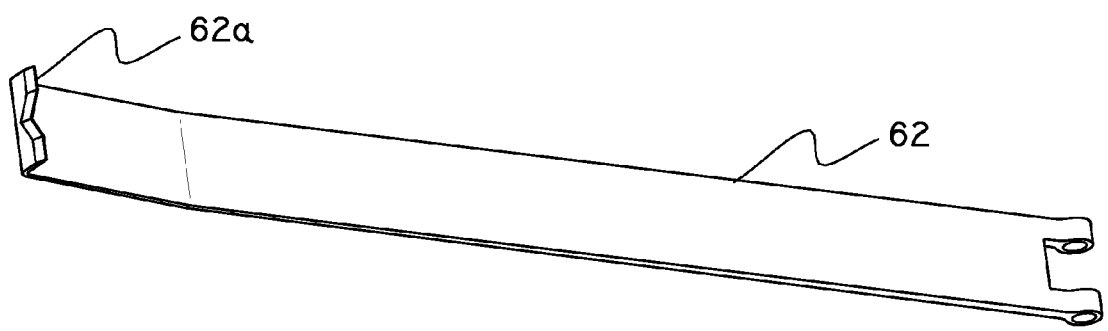
FIG. 25 illustrates a parting blade comprising a long arm with the blade to induce parting of the ribbon at one end bent to a right angle and the other end pivotally mounted to the trigger.

FIG. 24 shows the result of the action described above. The leftover piece of ribbon 36 simply stays with the deployed needle and wire block assembly 16.

Figure 30:
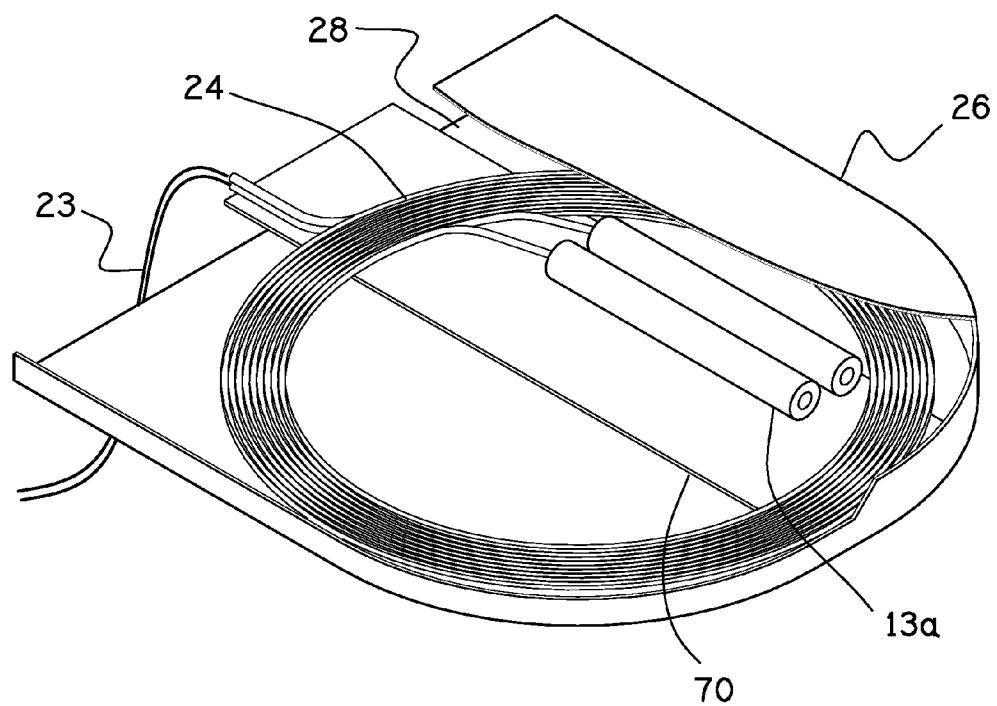
FIG. 30 is an isometric view of an individual shelf 28 in the cassette 26 illustrating a coiled extension 24 of insulated wire pair 23 disposed thereon.

FIG. 25 shows the complete parting blade 62, which in the illustrated embodiment has an elongated body having a right-angle bend at one axial extremity. That axial extremity has an engagement surface 62*a*. The other axial extremity is pivotally mounted to the trigger 22. FIG. 30 is an isometric view of an individual shelf 28 in the cassette 26 illustrating a coiled extension 24 of insulated wire pair 23 disposed thereon.

The wings 20 and 21 are disposed in parallel planes when the wings are in the gun. Thereafter, upon ejection from the gun the wings rotate to whatever angle is needed for each the respective wings to have planar face contact with the patient and specifically so that the respective wings have planar face contact with the skin of the patient on each side of a given needle electrode, and are thereafter rotated further to become parallel again, but 180 degrees from original, as they obscure the needles upon removal from the patient. Thus, the wings are almost coplanar as they rest nearly against each other, with needles obscured between, and held by the adhesive thereon.

Although the above description of various preferred embodiments emphasizes cartridges which support two parallel needle electrodes for simultaneous subcutaneous placement in the body of a patient, it will be understood by those skilled in the art that other embodiments may alternatively only implant a single needle electrode upon actuation of the trigger. The embodiments described above utilize a cartridge having cylindrical surfaces disposed at respective axial extremities thereof that engage respective parallel opposed channels in a track or slot. Other embodiments may change the gender of the coupling between the respective cartridges and the track or slot in which the cartridges move. For example, the respective cylindrical surfaces of each cartridge may have a slot that is dimensioned and configured for engaging respective rails on opposed sides of the track or slot.

The language used in the claims and specification to describe the apparatus of the present invention may use terms such as "barrel" and "magazine" to describe embodiments of the present invention because the terms facilitate description of the apparatus despite some material differences between the apparatus of the present invention and the typical apparatus in the firearms field where the term "barrel" usually refers to an elongated cylindrical element and the term "magazine" usually refers to a mechanism for holding a plurality of cartridges or shells. As used herein the term "barrel" refers to an elongated structure that directs one or more needle electrodes toward a patient. As used herein the term "magazine" refers to a structure for holding one or more needle electrode assemblies and intended for subsequent sequential placement in a patient.

In those embodiments of the present invention in which the sterile preloaded gun is sealed in a blister pack, the gun may be loaded with a fixture (not shown) that holds a plurality needle electrode assemblies in a rectilinear array aligned with the barrel. Other embodiments of the present invention utilize a magazine sleeve having an arcuate cross section holding a plurality of needle electrode assemblies whereby the loaded magazine may be inserted in the barrel of the assembly in substantially concentric relationship.

Figure 31:
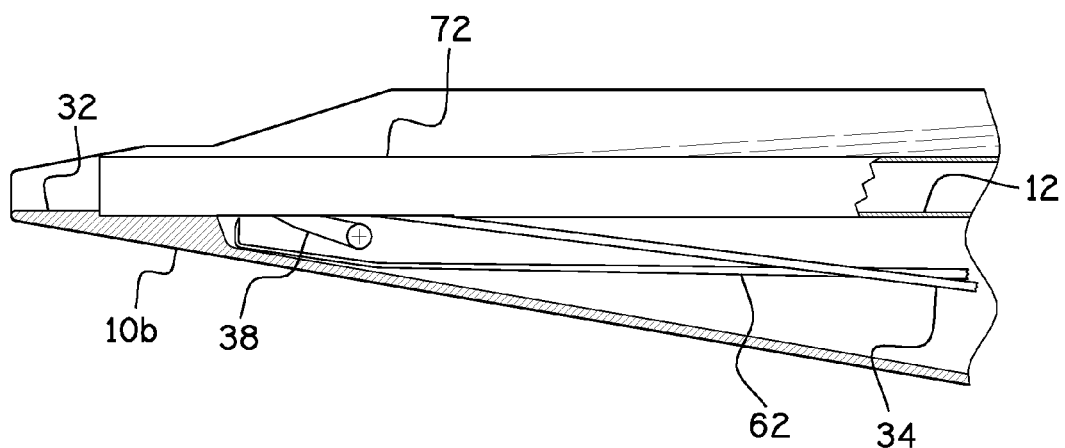
FIG. 31 is a cut-away side view of an alternate embodiment, in which needle assemblies are pre-loaded into a magazine, which is then slid all the way into the front end of the gun.

FIG. 31-FIG. 35 illustrate an alternate embodiment of the present invention. FIG. 31 is a cut-away side view of the alternate embodiment, in which needle assemblies are preloaded into a magazine, which is then slid all the way into the front end of the gun. The magazine 72 is fully inserted into the gun body 10b. The inside of the tubular magazine becomes the track 12, along which, the needle assemblies, not shown, are carried. The output deck 32, anti-backup pawl 38, ribbon parting blade 62, pusher rail(s) 34, and the rest of the gun body 10b remain exactly the same as the previously described embodiment.

Figure 32:
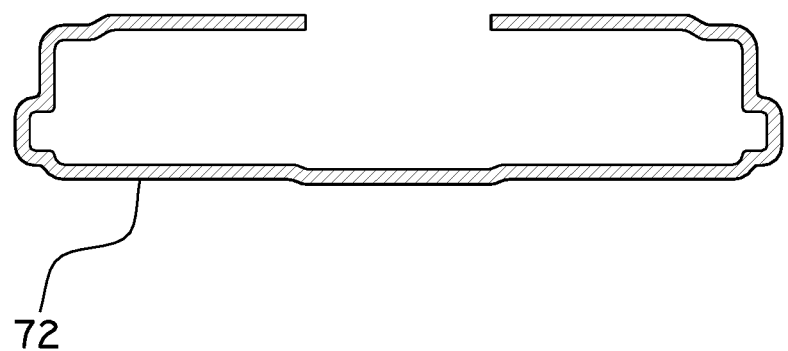
FIG. 32 is a scaled-up cross-section view the magazine of the alternate embodiment.
Figure 33:
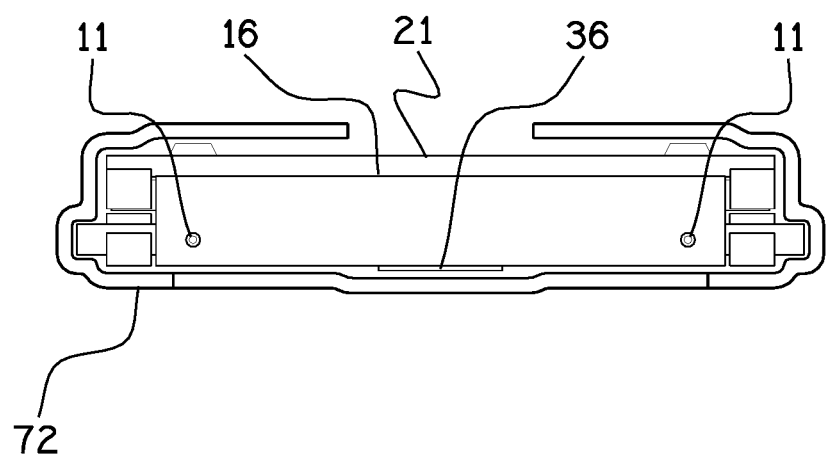
FIG. 33 is a scaled-up front-end view of magazine 72 of the alternate embodiment loaded with needle assemblies.
Figure 34:
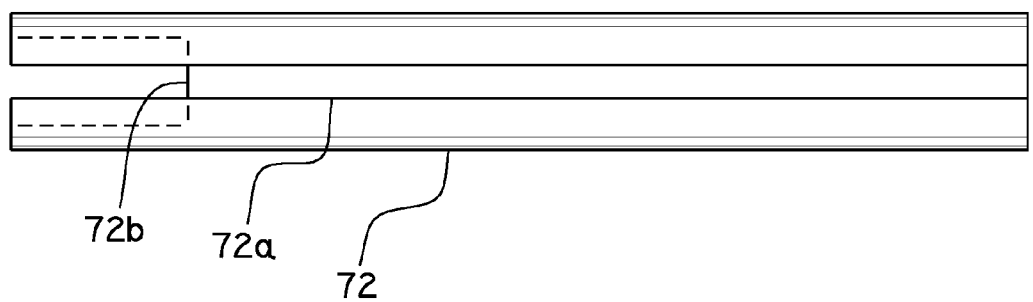
FIG. 34 is a top view of magazine 72 in the alternate embodiment, which runs the full length through the gun.

FIG. 32 is a scaled-up cross-section view of the magazine 72. FIG. 33 is a scaled-up front-end view of the magazine 72 loaded with needle assemblies. The viewer sees needle and wire block assembly 16, top wing 21, ribbon 36, and needle(s) 11. FIG. 34 is a top view of the magazine 72, which runs full length through the gun. Slot 72a (full length) accommodates the wire(s) 23 (still used, but not shown in this figure) of the previously described embodiment. Cutout 72b accommodates the pusher rail(s) 34 (still used, but not shown in this figure).

Figure 35:
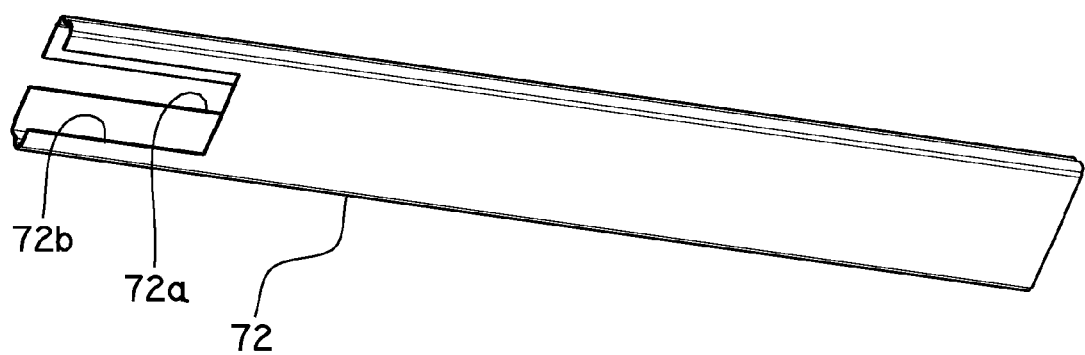
FIG. 35 is an isometric view of the bottom of magazine 72 in the alternate embodiment.

FIG. 35 is an isometric view of the bottom of the magazine 72. It more plainly shows the cutout 72b, which allows the pusher rail(s) 34, not shown, to get behind, and then push, the front-most needle assembly, not shown in this figure.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The previous description is provided to enable any person skilled in the art to practice the various embodiments described herein. Various modifications to these embodiments will be readily apparent to those skilled in the art, and the generic principles defined herein may be applied to other embodiments. Although the description above contains many specifics, these should not be construed as limiting the scope of the invention, but as merely providing illustrations of some of the presently preferred embodiments of this invention. Thus, the claims are not intended to be limited to the embodiments shown herein, but is to be accorded the full scope consistent with the language claims, wherein reference to an element in the singular is not intended to mean "one and only one" unless specifically so stated, but rather "one or more." Therefore, it will be appreciated that the scope of the present invention fully encompasses other embodiments which may become obvious to those skilled in the art, and that the scope of the present invention is accordingly to be limited by the appended claims, in which reference to an element in the singular is not intended to mean "one and only one" unless explicitly so stated, but rather "one or more." Furthermore, it should be understood that while the use of the word preferable, preferably, or preferred in the description above indicates that feature so described may be more desirable, it nonetheless may not be necessary and any embodiment lacking the same may be contemplated as within the scope of the invention, that scope being defined by the claims that follow. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary. All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A cartridge for cooperation with an associated neuromonitoring needle electrode placement gun which comprises:
   a housing;
   at least one elongated needle electrode having an axial extent and having a pointed axial extremity, said at least one elongated needle electrode being carried by said housing; and
   at least a first planar wing having first and second faces thereof, said first planar wing being carried by said housing and further including a second planar wing having first and second faces, said second planar wing being carried by said housing wherein said first and second planar wings are carried on said housing by a pivotal mounting dimensioned and configured to permit movement of said first and second planar wings to a position wherein said first and second planar wings are disposed in parallel overlapping relationship.

2. The cartridge as described in claim 1 wherein said first and second planar wings carried on said housing by a pivotal mounting dimensioned and configured to permit movement thereof to a position wherein said first and second planar wings are disposed in parallel overlapping relationship and said wings shield said respective pointed axial extremities to prevent either intentional or inadvertent contact with the respective pointed axial extremity of each of said elongated needle electrodes.

3. The cartridge as described in claim 1 wherein said first and second planar wings carried on said housing are movable to a position wherein said first and second planar wings are coplanar.

4. The cartridge as described in claim 3 wherein one side of each of said first and second planar wings is coated with a releasable adhesive suitable for simultaneous engagement with the skin of an associated patient.

5. Apparatus which comprises:
 a cartridge carrying first and second parallel spaced needle electrodes to permit monitoring spontaneous or electrically evoked myogenic activity, said cartridge including means for sliding engagement and cooperation with an associated neuromonitoring needle electrode placement gun and means for conducting electricity to said first needle electrode and means for conducting electricity from said second needle electrode.

6. the apparatus as described in claim 5 wherein each of said first and second needle electrodes have pointed axial extremities that abut a virtual line that is coplanar with and perpendicular to said electrodes.

7. The apparatus as described in claim 5 further including means for preventing needle sticks that includes a first planar wing carried by said housing.

8. The apparatus as described in claim 7 wherein said means for preventing needle sticks includes a second planar wing carried by said housing.

* * * * *